(12) United States Patent
Breitenstein et al.

(10) Patent No.: US 8,731,966 B2
(45) Date of Patent: *May 20, 2014

(54) SYSTEMS AND METHODS FOR REAL-TIME DATA INGESTION TO A CLINICAL ANALYTICS PLATFORM TO GENERATE A HEAT MAP

(75) Inventors: Agenta Breitenstein, Somerville, MA (US); Stanley Huang, Wellesley, MA (US); Donald Pettini, Andover, MA (US); Paul Bleicher, Boston, MA (US); Ryan Scharer, Somerville, MA (US); Hua Ye, Belmont, MA (US)

(73) Assignee: Humedica, Inc., Boston, MA (US)

( * ) Notice: Subject to any disclaimer, the term of this patent is extended or adjusted under 35 U.S.C. 154(b) by 172 days.

This patent is subject to a terminal disclaimer.

(21) Appl. No.: 12/890,018

(22) Filed: Sep. 24, 2010

(65) Prior Publication Data
US 2011/0077973 A1    Mar. 31, 2011

Related U.S. Application Data

(60) Provisional application No. 61/245,581, filed on Sep. 24, 2009, provisional application No. 61/249,305, filed on Oct. 7, 2009.

(51) Int. Cl.
| G06Q 10/00 | (2012.01) |
| G06Q 50/00 | (2012.01) |
| G06F 7/00 | (2006.01) |
| G06F 17/00 | (2006.01) |

(52) U.S. Cl.
USPC .................................................. 705/3; 705/2

(58) Field of Classification Search
USPC ......................................................... 705/2–3
See application file for complete search history.

(56) References Cited

U.S. PATENT DOCUMENTS

| 6,915,254 B1 * | 7/2005 | Heinze et al. ..................... 704/9 |
| 2001/0020229 A1 | 9/2001 | Lash |
| 2002/0073138 A1 * | 6/2002 | Gilbert et al. ................. 709/201 |
| 2002/0128861 A1 * | 9/2002 | Lau et al. ........................... 705/2 |
| 2003/0060688 A1 * | 3/2003 | Ciarniello et al. ............ 600/300 |
| 2004/0064341 A1 | 4/2004 | Langan et al. |
| 2004/0243438 A1 | 12/2004 | Mintz |

(Continued)

OTHER PUBLICATIONS

Clancy, Thomas R., "Managing Organizational Complexity: Putting It Altogether, Improving Performance in Heart Failure Outcomes", *JONA* vol. 39, No. 6 2009, 249-254.

(Continued)

*Primary Examiner* — Joy Chng
(74) *Attorney, Agent, or Firm* — GTC Law Group LLP & Affiliates

(57) ABSTRACT

The clinical analytics platform automates the capture, extraction, and reporting of data required for certain quality measures, provides real-time clinical surveillance, clinical dashboards, tracking lists, and alerts for specific, high-priority conditions, and offers dynamic, ad-hoc quality reporting capabilities. The clinical informatics platform may include a data extraction facility that gathers clinical data from numerous sources, a data mapping facility that identifies and maps key data elements and links data over time, a data normalization facility to normalize the clinical data and, optionally, de-identify the data, a flexible data warehouse for storing raw clinical data or longitudinal patient data, a clinical analytics facility for data mining, analytic model building, patient risk identification, benchmarking, performing quality assurance, and patient tracking, and a graphical user interface for presenting clinical analytics in an actionable format.

20 Claims, 25 Drawing Sheets

(56) References Cited

U.S. PATENT DOCUMENTS

| | | | |
|---|---|---|---|
| 2005/0228808 A1* | 10/2005 | Mamou et al. | 707/100 |
| 2006/0161456 A1* | 7/2006 | Baker et al. | 705/2 |
| 2007/0061393 A1 | 3/2007 | Moore | |
| 2007/0192143 A1 | 8/2007 | Krishnan et al. | |
| 2009/0089092 A1 | 4/2009 | Johnson et al. | |
| 2011/0077958 A1 | 3/2011 | Breitenstein et al. | |
| 2011/0077972 A1 | 3/2011 | Breitenstein et al. | |

OTHER PUBLICATIONS

De Ville, Barry, "Discover and Drive Brand Activity in Social Networks Paper 109-2009", *SAS Global Forum 2009 Data Mining and Predictice Modeling SAS Institute Inc.*, Cary, NC 2009, 1-13.

Fattore, Giovanni et al., "Social network analysis in primary care: The impact of interactions on prescribing behaviour", *Health Policy 92 (2009) journal homepage*: http://www.elsevier.com/locate/healthpol 2009, 141-148.

Keating, MD, Nancy L. et al., "Factors Affecting Influential Discussions Among Physicians: A Social Network Analysis of a Primary Care Practice", *2007 Society of General Internal Medicine 2007:22: 794-798 JIGM* Apr. 3, 2007, 794-798.

Luke, Douglas A. et al., "Network Analysis in Public Health: History, Methods and Applications", *Department of Community Health, School of Public Health, Saint Louis University* St. Louis, Missouri 63104 email:dluke@slu.edu Jan. 12, 2007, all.

"U.S. Appl. No. 12/889,904, Non-Final Office Action mailed May 8, 2012",, 20.

* cited by examiner

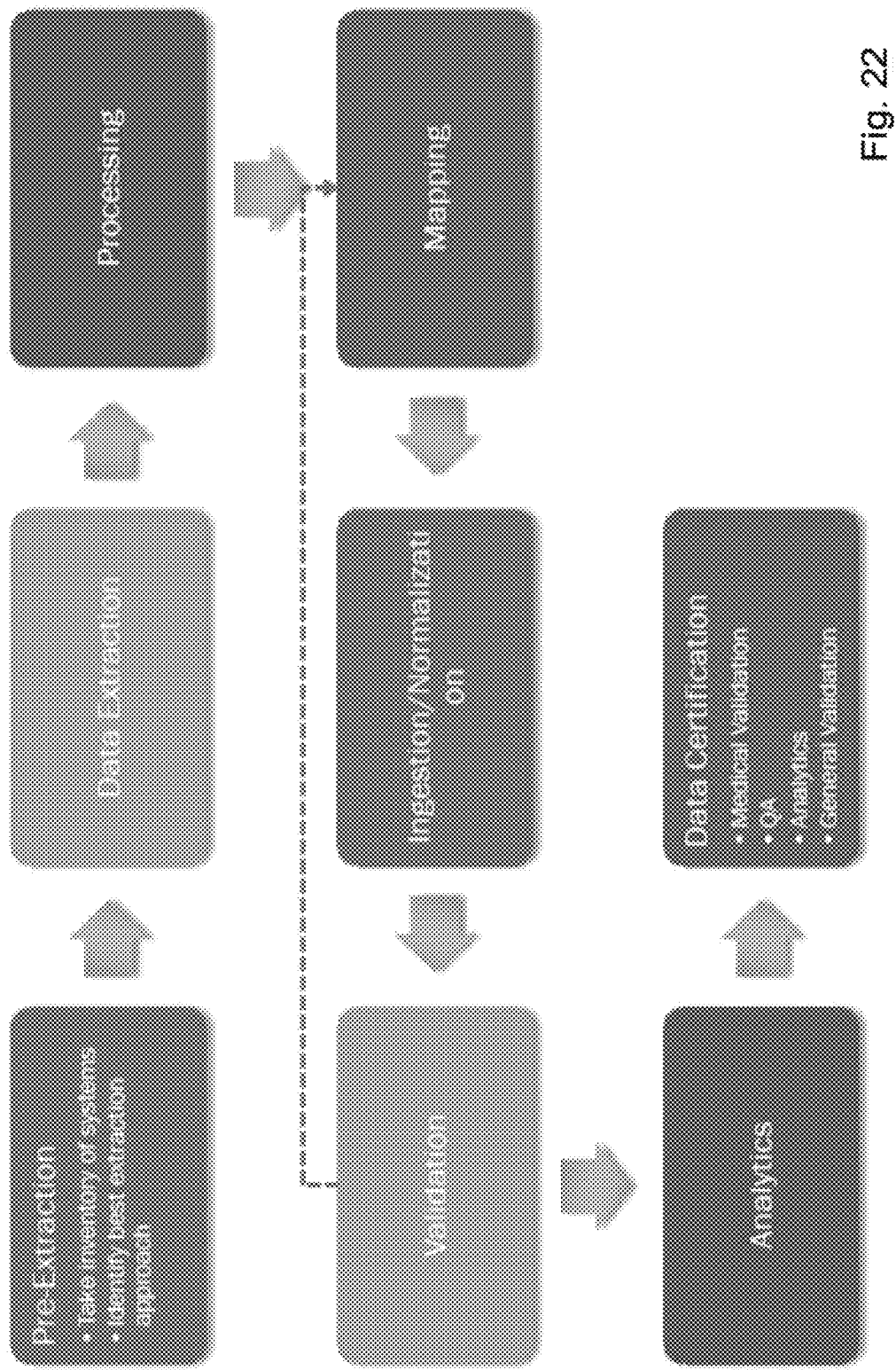

SYSTEMS AND METHODS FOR REAL-TIME DATA INGESTION TO A CLINICAL ANALYTICS PLATFORM TO GENERATE A HEAT MAP

CROSS-REFERENCE TO RELATED APPLICATIONS

This application claims the benefit of the following provisional applications, each of which is hereby incorporated by reference in its entirety:
U.S. Application Ser. No. 61/245,581, filed Sep. 24, 2009; and U.S. Application Ser. No. 61/249,305, filed Oct. 7, 2009.

BACKGROUND

1. Field

The present invention relates to clinical informatics, a clinical informatics platform and managing networks of health care providers.

2. Description of the Related Art

Health care systems are evolving at an unprecedented pace. While much remains uncertain, one thing is clear: knowledge is one key to success in times of change and uncertainty. The ability to meaningfully capture, report, and use data to deliver better and more cost-effective health care is critical. Value-based purchasing is making clinical performance improvement more important than ever. Success requires the ability to connect knowledge with action to improve performance.

There remains a need for a clinical informatics platform that automates the capture, extraction, and reporting of data required for certain quality measures; provides real-time clinical surveillance, clinical dashboards, tracking lists, and alerts for specific, high-priority conditions; provides improved methods and systems for analyzing and managing health care referral networks; and offers dynamic, ad-hoc quality reporting capabilities.

SUMMARY

The clinical analytics platform automates the capture, extraction, and reporting of data required for certain quality measures; provides real-time clinical surveillance, clinical dashboards, tracking lists, and alerts for specific, high-priority conditions; provides improved methods and systems for analyzing and managing health care referral networks; and offers dynamic, ad-hoc quality reporting capabilities.

In an aspect of the invention, a method of clinical tracking may include gathering healthcare data from a plurality of sources, processing the healthcare data, wherein processing comprises identifying, mapping and normalizing healthcare data elements, wherein the mapping comprises assigning data to a field of a database according to a hierarchically organized lexicon of healthcare data elements, wherein multiple data element entries in the lexicon are mapped to a single field for at least one field, analyzing the healthcare data to obtain at least one report, and presenting the report in a graphical user interface, wherein the report can be customized based on a criterion. The report may identify at least one risk relevant to at least one patient based at least in part on the gathered healthcare data. The report may include an alert relating to at least one risk associated with at least one patient based at least in part on the gathered healthcare data, such alert presented in at least one of an audible or visual manner. The report may include an alert identifying at least one patient care error and at least one recommendation for correcting such at least one error. The report may include instructions for the manner in which one or more healthcare providers are to provide care to one or more patients based at least in part on the gathered healthcare data. The report may identify a disparity between the available healthcare resources and the patient needs identified based at least in part on the gathered healthcare data. The report may identify a high-cost patient based at least in part on the gathered healthcare data. Processing the healthcare data also may include validating the healthcare data elements. The data may be gathered on a periodic basis. The data may be gathered on a real-time basis, the report may include instructions for the manner in which one or more healthcare providers are to provide care to one or more patients based at least in part on the gathered healthcare data and the report is updated on a real-time basis. The real-time basis may be at least as frequent as every five minutes. The graphical user interface may be presented via a software-as-a-service architecture. The report may relate to at least one of a patient, a medical care protocol, an outcome, a demographic, a behavioral risk factor, a disease risk factor, a procedure, a therapeutic, a therapeutic over a given time period, a risk level, a cost, an admission information, a utilization, readmission information, mortality, and a complication. The criterion may include at least one of a patient name, an issue, a physician, a location, a due by time for care or therapy, a risk level, a clinical measure, a procedure completed and an image taken.

In an aspect of the invention, a method of optimizing a healthcare resource plan may include gathering healthcare data relating to a plurality of patients from a plurality of sources, wherein the data are gathered on a periodic basis, processing the healthcare data, wherein processing may include identifying, mapping and normalizing healthcare data elements, wherein processing is repeated when new healthcare data may be gathered, wherein the mapping may include assigning data to a field of a database according to a hierarchically organized lexicon of healthcare data elements, wherein multiple data element entries in the lexicon are mapped to a single field for at least one field, analyzing the healthcare data to obtain at least one patient risk identification and patient tracking report, wherein analyzing is repeated when new healthcare data may be gathered and processed, and preparing a healthcare resource plan for care of the plurality of patients and optimizing the healthcare resource plan based on the data contained in the at least one patient risk identification and patient tracking report. The periodic basis may be in real-time. The real-time basis may be at least as frequent as every five minutes. Processing the healthcare data also may include validating the healthcare data elements. The method may further include re-optimizing the healthcare resource plan when new healthcare data may be gathered, processed, and analyzed. The method may further include re-optimizing the healthcare resource plan when a manual change is made to an element of the plan. The tracking report may relate to at least one of a patient, a medical care protocol, an outcome, a demographic, a behavioral risk factor, a disease risk factor, a procedure, a therapeutic, a therapeutic over a given time period, a risk level, a cost, an admission information, a utilization, readmission information, mortality, and a complication. Patients at risk may be automatically detected by the analysis and an alert is generated identifying such patients. High-cost patients may be automatically detected by the analysis and an alert is generated identifying such patients. The healthcare resource plan may be presented in a graphical user interface via a software-as-a-service architecture.

In an aspect of the invention, a method of comparative healthcare benchmarking may include gathering healthcare data from a plurality of sources, processing the healthcare data, wherein processing may include wherein processing may include identifying, mapping and normalizing healthcare data elements, wherein the mapping may include assigning data to a field of a database according to a hierarchically organized lexicon of healthcare data elements, wherein multiple data element entries in the lexicon are mapped to a single field for at least one field, analyzing the healthcare data to obtain at least one of a clinical, operational and financial benchmark, repeating the steps of gathering, processing, normalizing, and analyzing to obtain a data sample to compare with the at least one clinical, operational, or financial benchmark, wherein at least one change is made in at least one of the repeated steps, and presenting the data sample with the benchmark as a report in a graphical user interface, wherein the report can be customized by at least one of changing at least one criterion. The data may be gathered on a periodic basis. The data may be gathered on a real-time basis, such as at least as frequent as every five minutes. The plurality of sources may include sources relating to different geographic regions. The plurality of sources may include sources relating to different healthcare facilities. The plurality of sources may include sources relating to a specified geographic region. Processing the healthcare data also may include validating the healthcare data elements. The method may further include linking the healthcare data elements over time to form a longitudinal data record. The graphical user interface may be presented via a software-as-a-service architecture. The at least one criterion may be a data source, a time period, a chart type, a time interval for display, a time interval for analysis, a filter, a hospital, a physician, a patient, a patient characteristic, a cohort, a disease, a gender, an age group, a treatment, a payer type and an insurance provider.

In an aspect of the invention, a benchmarking and comparative analytics dashboard may include a clinical informatics facility, including a data extraction facility that gathers clinical data from numerous sources, a data mapping facility that identifies and maps key data elements and links data over time, wherein the mapping may include assigning data to a field of a database according to a hierarchically organized lexicon of healthcare data elements, wherein multiple data element entries in the lexicon are mapped to a single field for at least one field, a data normalization facility to normalize the clinical data, a flexible data warehouse for storing raw clinical data or longitudinal patient data, and a clinical analytics facility for data mining and analytic model building, a user selectable dashboard definer configured to provide user selectable options for defining the clinical analytics to be presented in a report at a dashboard, and a display definer configured to operate in conjunction with the user selectable dashboard definer to define the format in which the clinical analytics report from the clinical informatics facility is to be presented at the dashboard. The data may be gathered on a periodic basis. The data may be gathered on a real-time basis. The real time basis may be at least as frequent as every five minutes. The data normalization facility may de-identify the data. The method may further include validating the clinical data. The clinical analytics facility may enable patient risk identification and patient tracking The selectable options may include the addition of a comparative benchmark. The selectable options may enable comparison to at least one of another patient, healthcare provider, doctor, healthcare facility, hospital, disease, condition, gender and age group. The selectable options may include the addition of a patient risk identification and patient tracking report relating to at least one of a patient, medical care, an outcome, a demographic, a behavioral risk factor, a disease risk factor, a procedure, a therapeutic, a utilization, a readmission, mortality, and a complication. The format of the report may include at least one of a table, a chart, text, and a graph and the format may be customized based on at least one of a data source, a time period, a chart type, a time interval for display, a time interval for analysis, a filter, a hospital, a physician, a patient, a patient characteristic, a cohort, a disease, a gender, an age group, a treatment, a payer type and an insurance provider. The dashboard may be presented via a software-as-a-service architecture.

In an aspect of the invention, a method of ingesting and analyzing healthcare data from a plurality of data sources in real-time may include connecting to at least one data source, retrieving data from the data source on a periodic basis to a database, synchronizing data between the at least one data source and the database, processing the data to identify data elements, map data elements, and normalize data elements, wherein the data elements are stored in a database, wherein the mapping may include assigning data to a field of a database according to a hierarchically organized lexicon of healthcare data elements, wherein multiple data element entries in the lexicon are mapped to a single field for at least one field, linking the data elements over time to form a longitudinal data record, wherein the longitudinal data records are stored in a longitudinal data warehouse, and analyzing the at least one of the data elements and data records to obtain at least one of actionable clinical analytics, a patient risk identification, a disease-specific analytic model, a predictive model, a benchmark and a quality measure. The periodic basis on which data are retrieved may be real-time. Real-time may be at least as frequent as every five minutes. The at least one data source may include doctor's notes from which data may be retrieved using natural processing language. The at least one data source may include at least one of an electronic medical record, an electronic health record, ambulatory clinical data, claims data, paid claims data, adjudicated claims data, inpatient clinical data, pharmacy data, doctor's notes, self-reported data, census data, telemetry data, a networked monitor, a home blood pressure device, a home health monitoring device, a sensor device, mortality data, an internal management system, a hospital inventory system, a clinical inventory system, a clinical guideline, a specialty management system and an order set. Processing the healthcare data also may include validating the healthcare data elements. The at least one of actionable clinical analytics, a patient risk identification, a disease-specific analytic model, a predictive model, a benchmark and a quality measure may be presented in a graphical user interface via a software-as-a-service architecture.

In an aspect of the invention, a clinical informatics platform may include a data extraction facility that gathers clinical data from numerous sources on a periodic basis, a data mapping facility that identifies and maps key data elements and links data over time, wherein the mapping may include assigning data to a field of a database according to a hierarchically organized lexicon of healthcare data elements, wherein multiple data element entries in the lexicon are mapped to a single field for at least one field, a data normalization facility to normalize the clinical data, a flexible data warehouse for storing at least one of the raw clinical data and longitudinal patient data, a clinical analytics facility for data mining, analytic model building, patient risk identification, and patient tracking, and a graphical user interface for presenting clinical analytics in an actionable format. The periodic basis on which data are gathered may be in real-time. Real-time may be at least as frequent as every five minutes. The numerous sources may include doctor's notes from which data may be retrieved using natural processing language. The numerous sources may include at least one of an electronic medical record, an electronic health record, ambulatory clinical data, claims data, paid claims data, adjudicated claims data, inpatient clinical data, pharmacy data, doctor's notes, self-reported data, census data, telemetry data, a networked monitor, a home blood pressure device, a home health monitoring device, a sensor device, mortality data, an internal management system, a hospital inventory system, a clinical inventory system, a clinical guideline, a specialty management system and an order set. The data normalization facility may de-identify the data. The method may further include validating the clinical data. The graphical user interface may be presented via a software-as-a-service architecture.

In another aspect of the invention, a computer readable medium having code which implements a method for describing, evaluating, understanding, or managing a network of health care providers, the method may include constructing a referral network database of physicians and health care providers from at least one of a private and a public data source, extracting data pertaining to shared patients or referrals between the physicians and health care providers from a database, and generating a graphical representation of referral patterns in the referral network of physicians and health care providers, wherein at least one element of the graphical representation depicts a measure of an extent of a type of activity within the referral network. The element of the graphical representation may use at least one of size, thickness, color and pattern to depict a type of activity. The element of the graphical representation may depict how many patients are shared among at least two health care providers. The medium may further comprise analyzing the referral patterns in the graphical representation to examine characteristics of the practice of the network and to enable managing the network of health care providers. The step of constructing a referral network of physicians and health care providers may use data mining techniques to find relationship data between physicians and health care providers. The step of constructing a referral network of physicians and health care providers may identify physicians and health care providers as nodes with linkages in a referral network. The data sources may include automated collection and user-generated data sources for referral network construction. The user-generated data may be from a survey. The data pertaining to shared patients or referrals may be extracted from a claims or electronic health record database. The graphical representation may be an x-y coordinate system, an xyz coordinate, a pie chart, a radar display, a GIS map, and other non-xy plots. Groups of physicians and health care providers may be differentiated in the graphical representation by at least one of a color, a shape, a shading, and a size. The size of the object representing the physicians or health care providers in the graphical representation may correlate with a metric. The metric may be at least one of cost, quality of care, compliance, or other measure of medical care, cost, resource use, quality or patient outcome.

These and other systems, methods, objects, features, and advantages of the present invention will be apparent to those skilled in the art from the following detailed description of the preferred embodiment and the drawings.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

BRIEF DESCRIPTION OF THE FIGURES

The invention and the following detailed description of certain embodiments thereof may be understood by reference to the following figures:

FIGS. 3a-3b depict a data processing and clinical surveillance tool of the clinical informatics platform.

FIG. 20 depicts a COAG Risk group tracking dashboard.

FIG. 22 depicts a block diagram of the data life cycle.

DETAILED DESCRIPTION

Figure 1A:
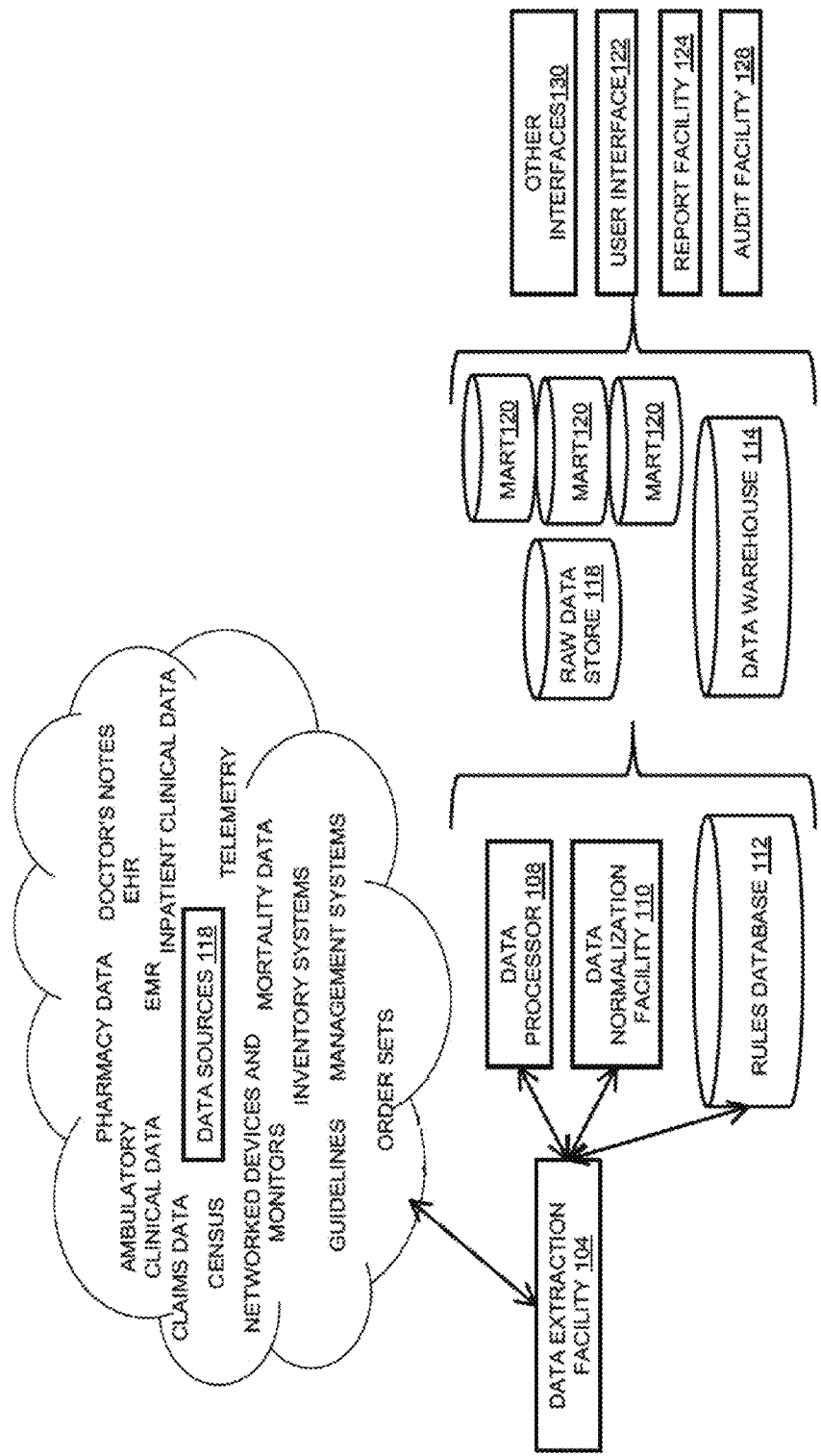
FIG. 1a depicts a block diagram of the clinical analytics platform.

The clinical analytics platform automates the capture, extraction, and reporting of data required for certain quality measures, provides real-time clinical surveillance, clinical dashboards, tracking lists, and alerts for specific, high-priority conditions, provides improved methods and systems for analyzing and managing health care referral networks, and offers dynamic, ad-hoc quality reporting capabilities. Throughout this specification, real-time indicates that an action is taken in an interval of time such that the data that are available to the platform 100 are data that are current as of an interval of time not far from the current time. The interval can vary from a few hours or minutes, such as five minutes, all the way to instantaneous.

The clinical informatics platform may empower health care, pharmaceutical and biotechnology firms, medical device manufacturers, government agencies, and financial services firms with insight into how to manage provider networks and provider network shared patients or referrals, how patient populations are treated, which treatments and procedures are prescribed, and importantly, the quality, efficacy, and cost of this care. The clinical informatics platform may assemble, standardize, and analyze clinical, operational, social network, referral, insurance and financial data across varied treatment settings and time periods to generate a longitudinal, comprehensive view of patient care. The clinical informatics platform may address the specific needs of inpatient and outpatient health care providers, pharmaceutical and biotechnology firms, medical device manufacturers, government agencies, and financial services firms by combining deep, retrospective capabilities with powerful real-time predictive tools that connect knowledge with action.

The clinical informatics platform may enable organizations to transform an immense reservoir of data into valuable, actionable knowledge using a comprehensive suite of software-as-a-service (SaaS) solutions that unlock the clinical information needed to improve patient care while improving financial performance. The SaaS-based clinical informatics platform applies sophisticated techniques to mine, standardize, validate and/or aggregate health care data from disparate IT systems, all within a state-of-the-art, HIPAA-compliant, and highly secure environment. The clinical informatics platform analyzes clinical, operational, social network, referral, insurance and financial data and delivers powerful analytic insights and comparative benchmarks with cost-effective, retrospective, and real-time SaaS-based tools. The SaaS-based tools enable delivering real time comparative analytics without the end user having to purchase or maintain any additional hardware or human resources and includes rapid, scalable, data extraction, mapping, and ontological normalization systems. The clinical informatics platform may combine both retrospective, deep-dive analytic systems, such as the benchmarking and analytics tool 202 or the data processing and clinical surveillance tool 302, with real-time data processing capabilities. In embodiments, the platform may be modular and contain all available tools or only certain tools. The clinical informatics platform may include disease-specific analytic tools, predictive models, and modules. The clinical informatics platform may include or enable the generation of detailed, customizable clinical, operational, social network, referral, insurance and financial benchmarks. The clinical informatics platform may support collaborative development and testing of performance and operational improvement strategies within and among organizations.

The historic barriers to leveraging health care, referral, insurance and social networking data are many: data reside in many different systems, data are trapped in local terminologies and free text, robust clinical models require costly tools and large samples, and real-time clinical analytics are costly and difficult-to-use, to name a few. The needs are clear: extract all the data, normalize all the data, provide robust clinical and networking analytics, and deliver powerful and timely insights. The clinical analytics platform meets these needs: it has flexible, platform-agnostic data extraction capabilities, provides scalable data normalization and next-generation natural language processing (NLP), a singular, relational longitudinal patient data warehouse, real-time predictive analytics, modeling, patient tracking tools, social networking and referral analysis tools, and clinical checklists. With the tools available in the clinical informatics platform, users may: gain valuable insight into the clinical and operational performance of an organization; conduct real-time and retrospective analytics and benchmark clinical performance; and employ disease-specific clinical analytics and evidence-based data to intervene in a timely manner to identify patients at risk, reduce morbidity, mortality, and complications in real-time, ensure that opportunities for improvement are identified before the patient has left the care setting, and, and manage provider networks and provider network shared patients or referrals, and otherwise effect positive change.

An understanding of all aspects of clinical and operational performance, such as the quality, safety, and cost of healthcare provider care, may be enabled by the clinical informatics platform. The health care provider may be enabled to act in real-time to ensure delivery of the best and most efficient care. Health care providers may be enabled to compare, analyze, and identify best practices, and then collaborate with peers around the development and dissemination of best practices and to optimize performance-based reimbursement. The clinical informatics platform may connect cost and outcomes to maximize cost-effective care, identify and track the care of high-cost and high-risk patients in real-time to reduce preventable complications and/or never events, and improve performance on Joint Commission (JCAHO) and pay-for-performance measures, and prove the value of the care delivered to payers with customizable, comparative performance benchmarks. Health care providers may be empowered to qualify for certain government and private programs, such as the American Recovery and Reinvestment Act (ARRA) funding.

Referring to FIG. 1a, a block diagram of the clinical analytics platform 100 is shown. A data extraction facility 104 can extract data from a plurality of disparate, healthcare and claims data sources 118 to enable the real-time collection, processing and centralized storage of health records in a database. Data ingestion techniques may be applied to a heterogynous system of EMRs from various vendors and systems to obtain data, normalize them and store the newly processed data in a homogenous database where a single set of applications can be used to interface with and analyze the data. Real-time, continuous data ingestion may come from various data sources 118 which may include ambulatory clinical data, pharmacy data, doctor's notes, EHRs, EMRs, inpatient clinical data, biographical data, hospital billing data, claims data, census data, self-reported data, networked devices and monitors (e.g. blood pressure device, glucose meter, etc.), mortality data, telemetry, inventory systems, clinical guidelines, management systems, order sets, and the like. For example, NLP techniques can be used to gather data from doctor's notes or other transcriptions, both numeric and text data. Data may be extracted, optionally encrypted, and ingested by the system in a running load process. Data may be obtained through an RSS feed or a transmission or extraction of data in a format such as XML, HL7, SCRIPT, X12, CSV, HL7v2, HL7v3, Dicom, X12N, NCPDP, and the like. Extract, Transform, and Load (ETL) tools may be used to connect remote databases to the platform 100 and pull data out of the remote databases so that the data goes from database to database. This method speeds things up and requires less hardware since a copy of the data does not have to be written for transmission or extraction.

The platform 100 enables ingestion and semantic normalization of the healthcare data by converting the data in the healthcare records to standardized data elements using a data normalization facility 110 and mapping the converted data with standard terminologies, such as Federal Health Architecture (FHA) terminologies, billing codes, IDC codes, CPT codes and the like using a mapping application of the data processor 108. The data processor 108 may transform data from the various formats in which it exists. Data may be mapped iteratively against divergent source systems. Mapping data may take advantage of standard and custom terminologies and combinations thereof. For example, the terminologies may enable identifying data elements by the various ways they may be described in different data sources and mapping all of the disparate elements to a single terminology used by the platform 100. In another embodiment, mapping may be ontological, that is, the terminologies may have a hierarchy. For example, 5 different variables may be found in a single or a plurality of data sources. In choosing which target variable of the platform to map the 5 variables to, a terminology may be consulted. Multiple possibilities may exist in the terminology, but a hierarchy of the terminologies may facilitate choosing which target variable of the platform to use. A rules database 112 may be used for storing terminologies, codes, hierarchies, rules for data de-identification, and the like. The rules database 112 may be updated periodically as new terminology becomes available or updated. The rules database 112 may provide rules to the data processor 108 for mapping. The rules database 112 may also store rules, attributes, characteristics, and criteria that are used in each analytic model.

Data may be linked over time to create longitudinal patient records. Data may also be linked along the lines of cohorts, practice groups, geographic areas, and the like. The data may be subject to validation. Validation may include identifying and omitting outlier values from the data, removing unreliable data and the like.

The data may be stored in a flexible data warehouse, such as a raw data store 118, data mart 120 or a longitudinal patient data warehouse 114.

The data may be analyzed by the data processor 108. Since the data may be real-time or near real-time, the analysis can enable providing care instructions, flagging medication and/or care errors, flagging events for follow-up or treatment, making recommendations, supporting disease management, cost containment, generate epidemiological/bioterrorism alerts, and the like. Real-time data ingestion, processing, and analysis enables automating processes and generating and updating care plans in near real time. The data may be certified. Interfaces to the platform 100, such as a user interface 122, report facility 124 audit facility 128, and other interfaces 130, may be used to search and view data, initiate analyses, visualize data, generate reports, generate a tracking page, and the like.

Figure 1B:
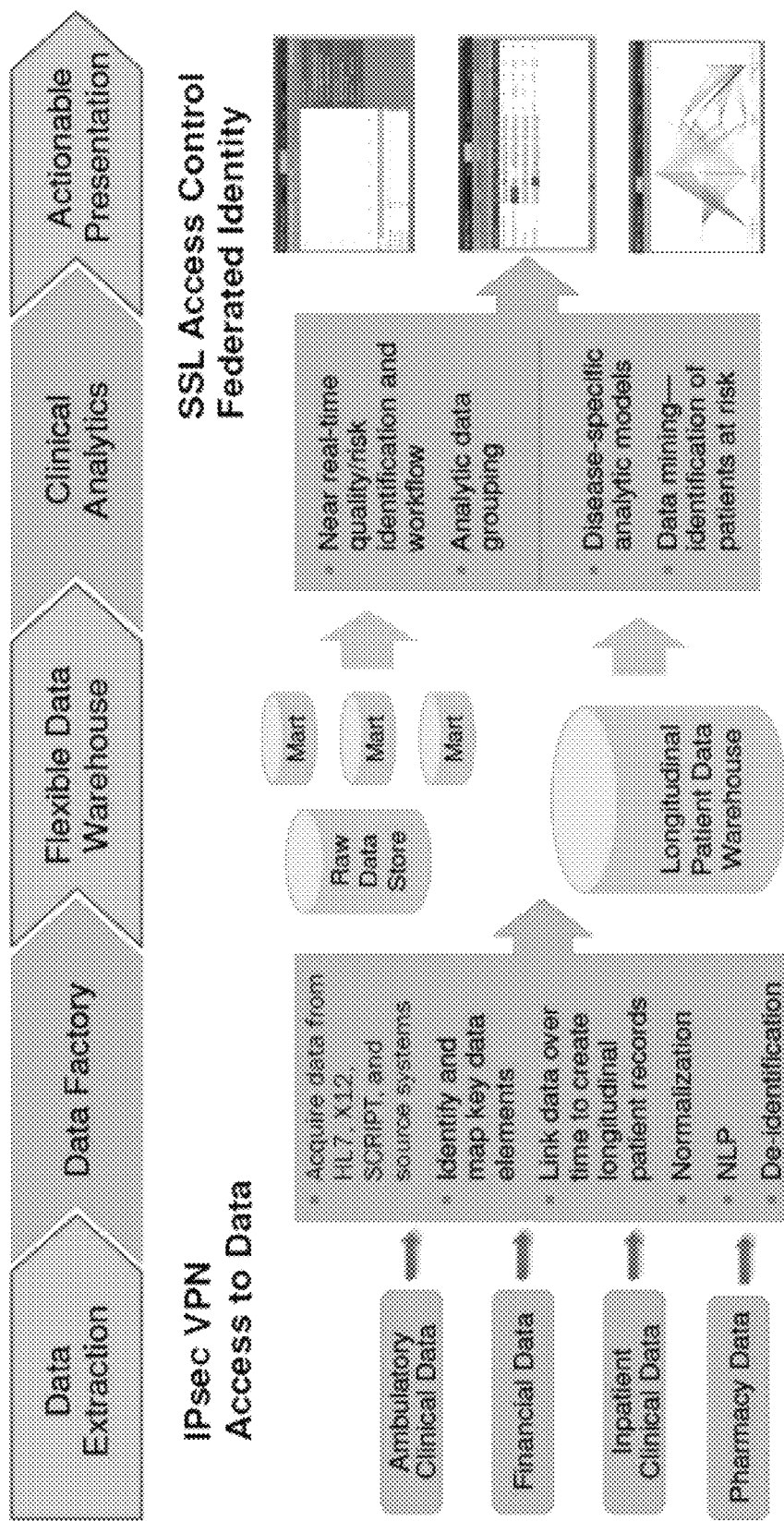
FIG. 1b depicts a workflow of the clinical analytics platform.

In a workflow of the clinical informatics platform as shown in FIG. 1b, data, such as ambulatory clinical data, financial data, inpatient clinical data, pharmacy data, and the like, may be gathered and/or extracted from source systems. The extracted data may undergo manipulations, such as mapping and normalization prior to storage in a database. The data may then be analyzed, tracked, manipulated and the like by any number of clinical analytics tools. The analytics may be modular, such as by disease, condition, cohort, patient area, geographic area, therapeutic protocol, practice group, hospital, and the like. The analytics may generate granular comparative data. The analytics may enable predictive modeling and understanding of the cost and efficiency of care. The analytics may enable quality measures, such as PQRI and HEDIS registry reporting. For example, a clinical analytics tool may enable analytic data grouping. FIG. 22 depicts a block diagram of the data life cycle including the following steps: pre-extraction where inventory is taken of systems and the best extraction approach is identified, data extraction, processing, mapping, ingestion, normalization, validation, analytics, and data certification, such as medical validation, QA, analytics and general validation.

In an embodiment, the platform 100 may comprise tools for analysis and data presentation and reporting. Certain tools may enable near real-time quality/risk identification and workflow. Tools may enable disease-specific analytic models. Tools may enable data mining, such as to identify patients at risk. In any of these tools, the analytics may be presented as an actionable visualization that may highlight variance. The presentation may include patient, physician, group views, and the like. The data presentation may be a collaboration platform. The data presentation may include real-time alerts, such as alerts relating to at least one risk associated with at least one patient based at least in part on the gathered healthcare data. Alerts may be presented in at least one of an audible or visual manner. In an embodiment, data presentation may be flash-based or involve some other dynamic media and/or animation.

Referring to FIG. 2, the clinical informatics platform may comprise a tool for enabling robust clinical, operational, and financial benchmarking and comparative analytics across the continuum of health care. The benchmarking and analytics tool 202 may be a dashboard for presenting comparative analytics. Data from disparate data sources 118 are extracted as described herein, normalized and mapped as described herein, then analyzed to obtain a benchmark and a data sample to compare to the benchmark. In some embodiments, the benchmark is known and does not have to obtained through analysis.

The analytics may be presented in a number of report formats, such as tables and graphs. The graphs may be of any format, such as bar graph, pie chart, scatter plot, line graph, and the like. The graphs may be customized using a number of built-in features of the tools, such as by changing the data source, the time period for analysis, the chart type, time intervals for display, a custom or built-in filter, a comparison to another subject (such as hospital, physician, disease, gender, age group, and the like), and the like. A graphical user interface to the platform 100 may be used to present the comparative data and the benchmark as a report.

Figure 2A:
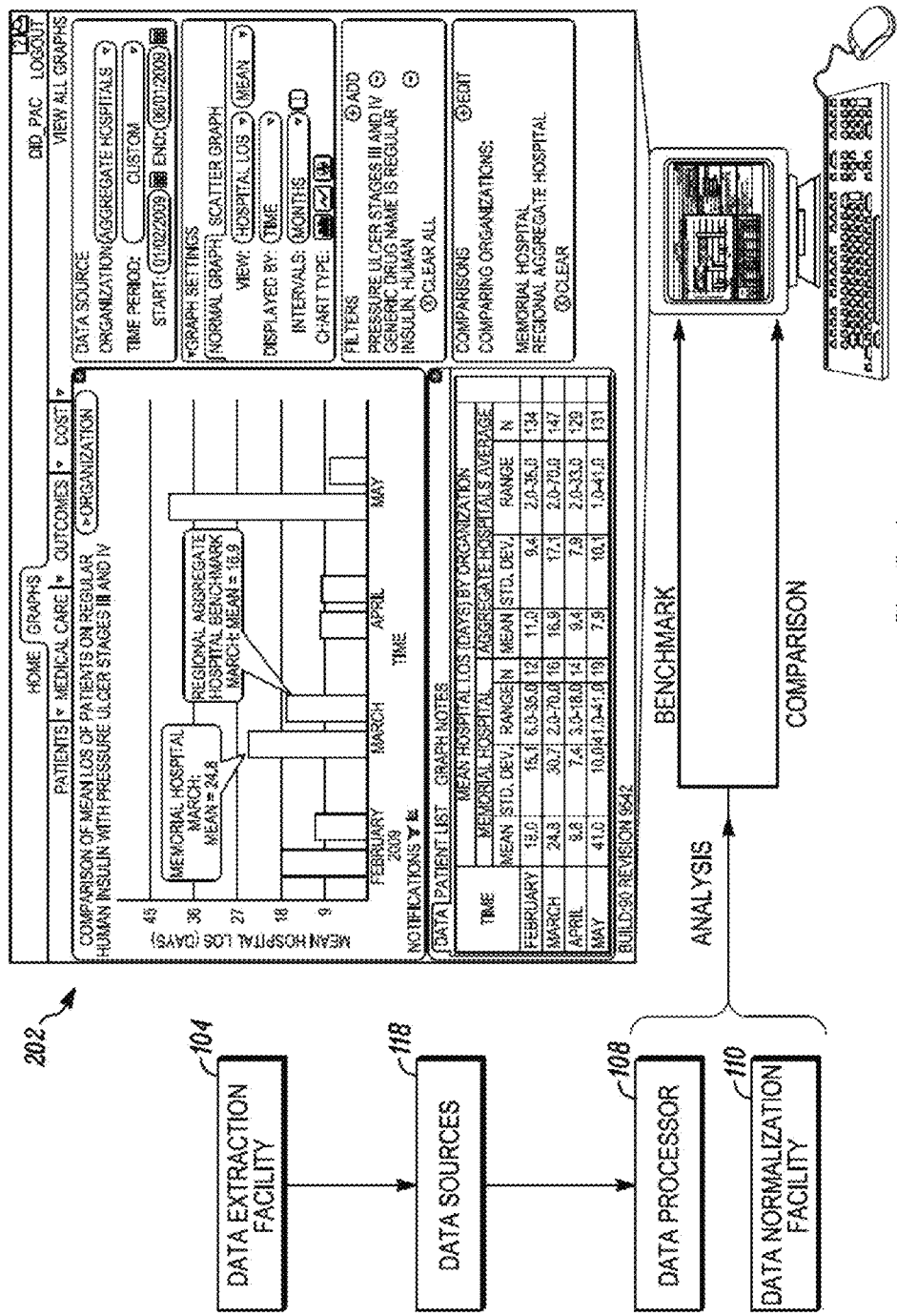
FIGS. 2a-2b depict a benchmarking and analytics tool of the clinical informatics platform.
Figure 2B:
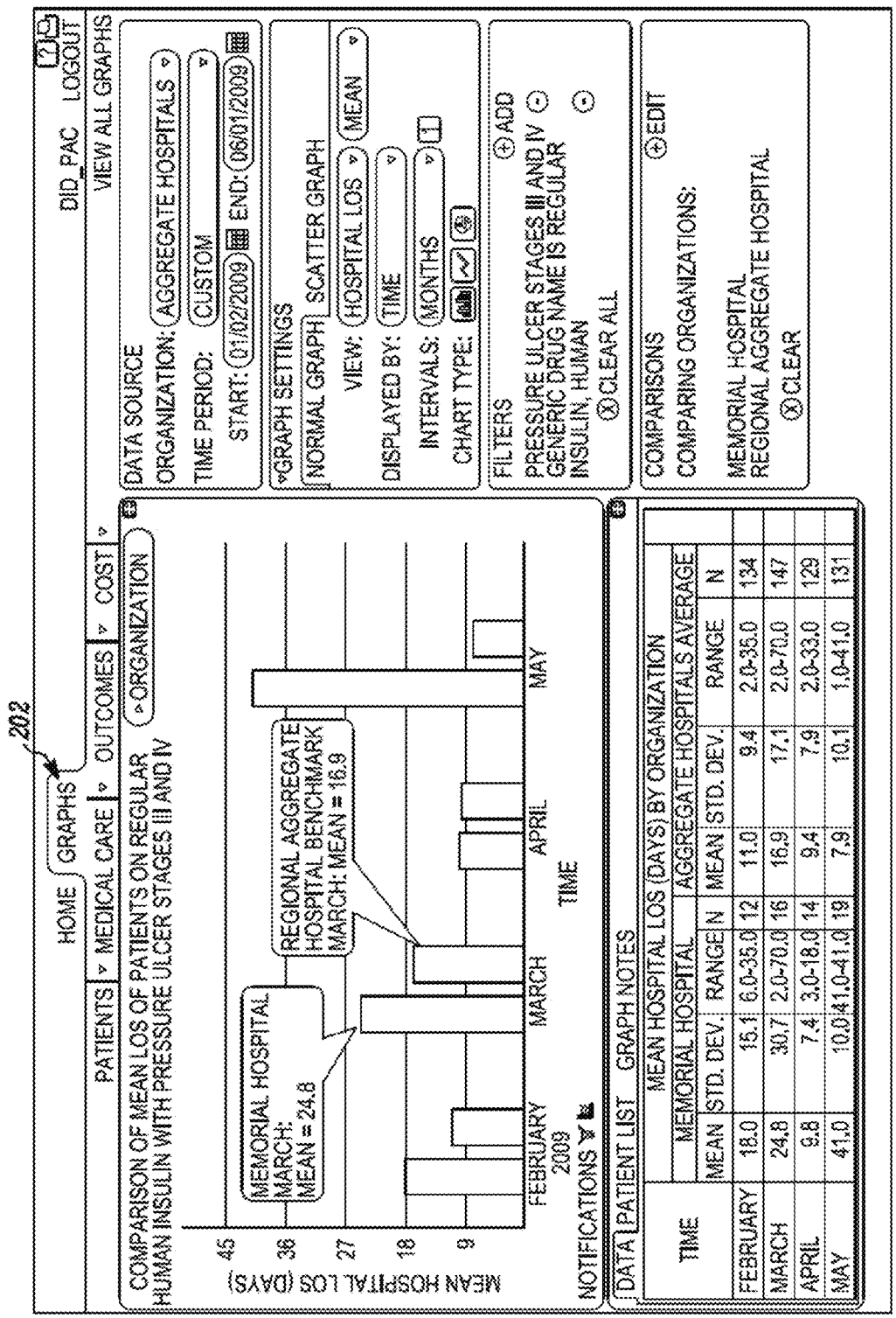

For example, the chart 202 in FIG. 2a, shown expanded in FIG. 2b, shows medical care analytics in the field of utilization. FIG. 2b depicts a chart that compares the mean length of stay (LOS) of patients on regular human insulin with pressure ulcer stages III and IV, with the mean hospital LOS on the y-axis and the time period on the x-axis. In this graph, the mean LOS for one hospital is compared to a regional aggregate hospital benchmark. A filter may be applied to this chart, such as by using a filter wizard. For example, the data may be filtered by insurance provider so that LOS is displayed for particular insurance providers, such as MEDICARE, MEDICAID, MEDICARE and MEDICAID, private insurance, government-sponsored insurance, and the like. To enable a different comparison, a comparison wizard may be employed. For example, a Charlson co-morbidity index comparison may be requested for the data. Instead of having a single data point, the data may be presented for each time interval by Charlson index or by range of Charlson indices. In another example, the data may be compared to another hospital including to or instead of the benchmark. In yet another example, the data may be presented at a more granular level, such as by attending physician, hospital floor, hospital unit, hospital bed, procedures, and the like. By providing different ways to present and manipulate data, patterns and outliers may be more readily identified. The visual dashboard provides a number of benefits. It enables real-time clinical intervention and reduces cost, morbidity, and mortality. It gathers, maps, and normalizes data in near real-time to predict and track which patients are likely to be high-risk and/or high cost and to alert for compliance to Joint Commission Core Measure metrics.

Figure 3A:
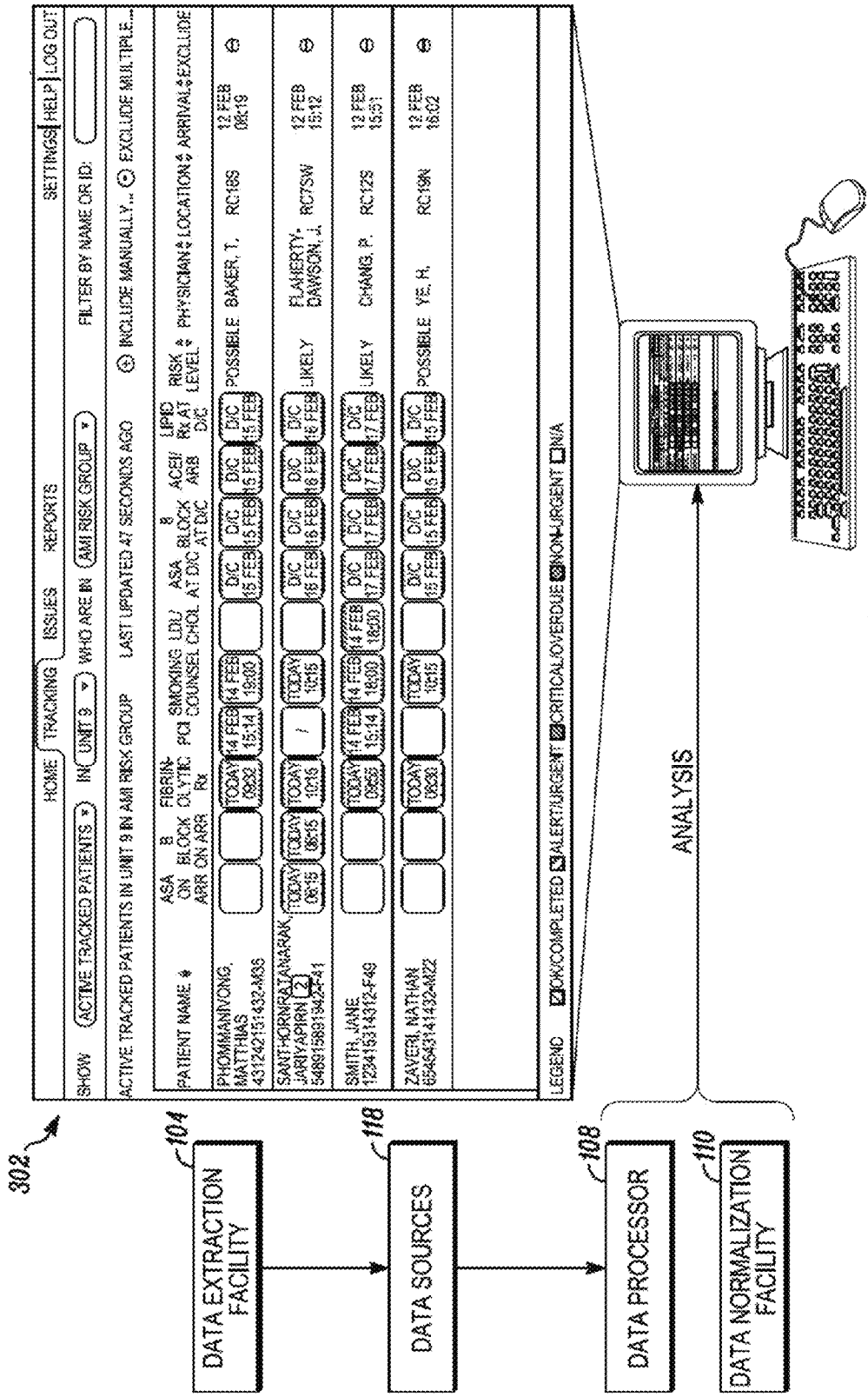
Figure 3B:
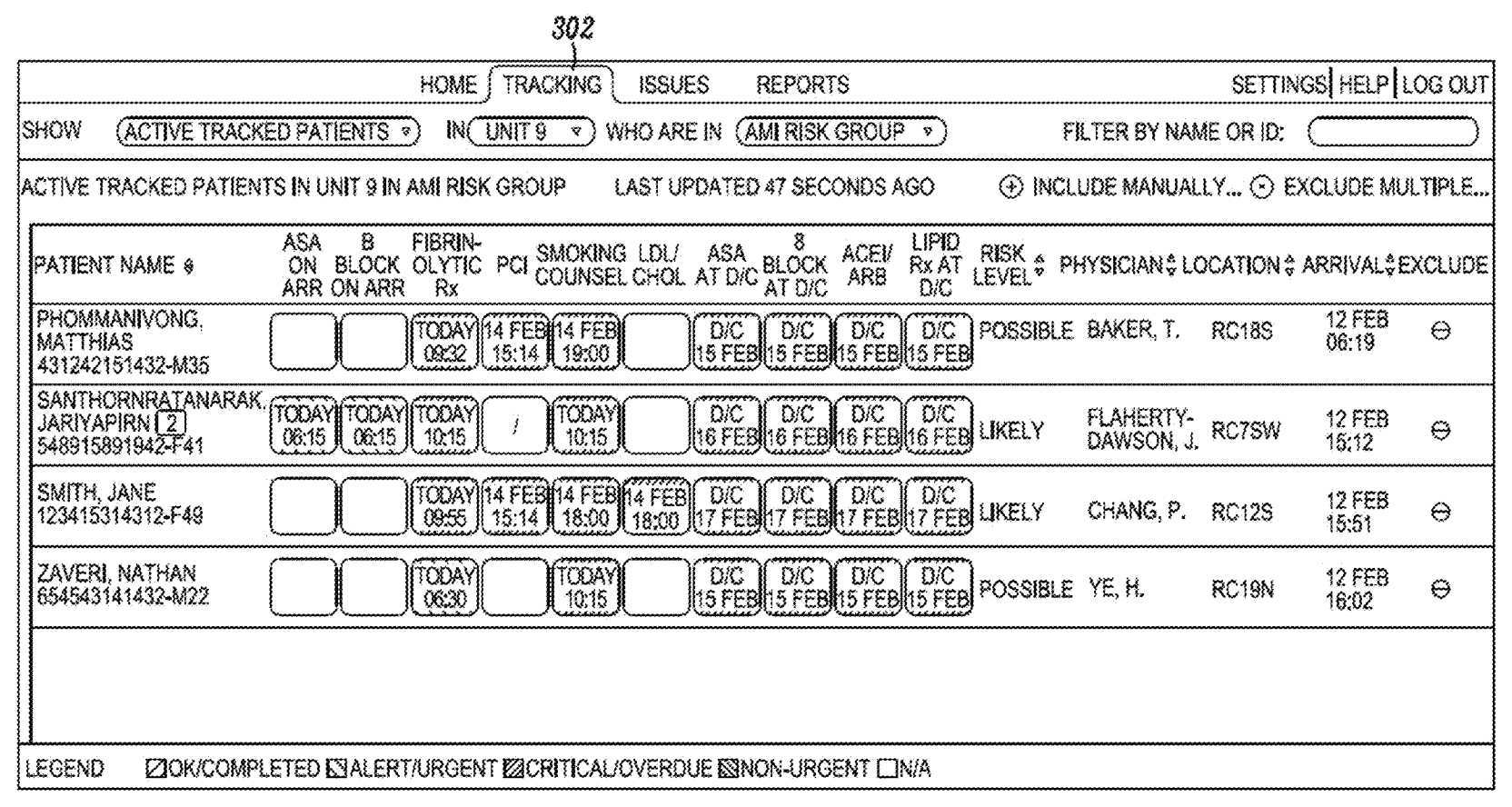
Figure 19:
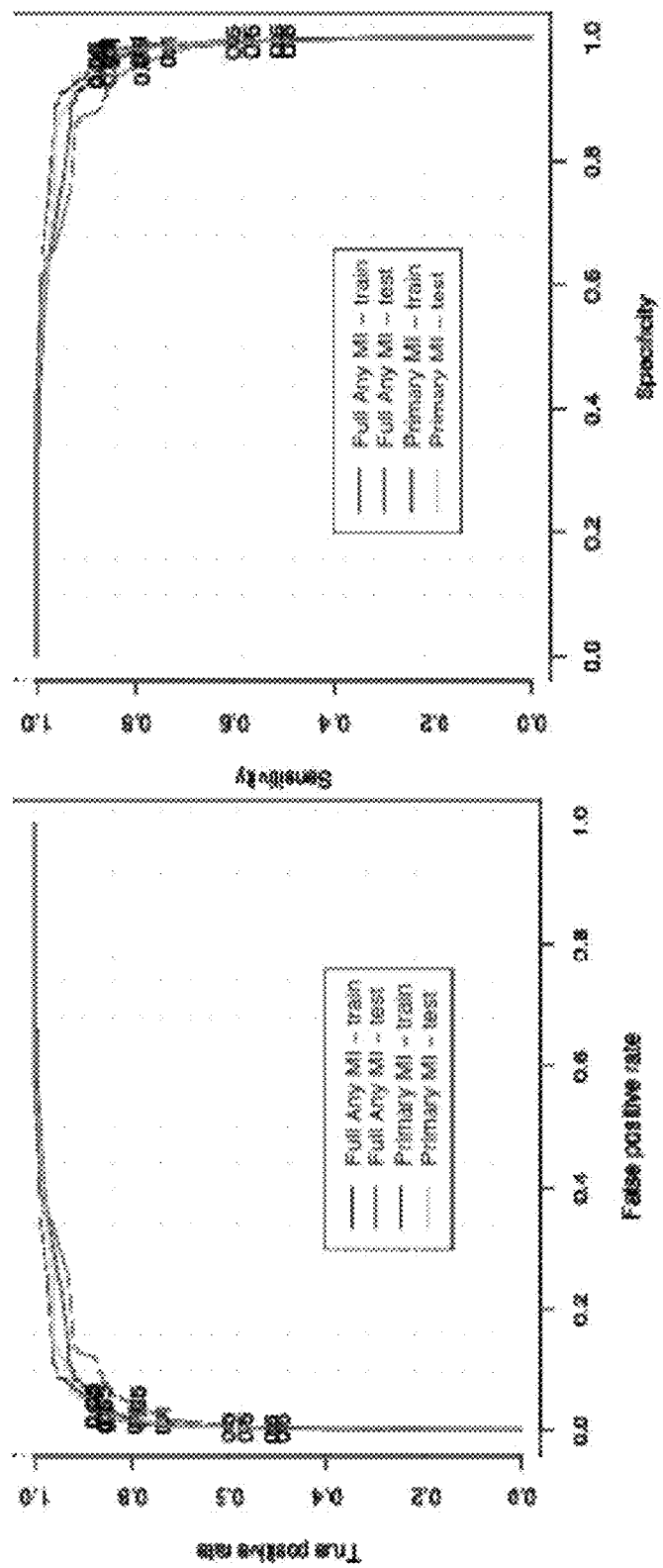
FIG. 19 depicts the output of an AMI detection algorithm.
Figure 20:
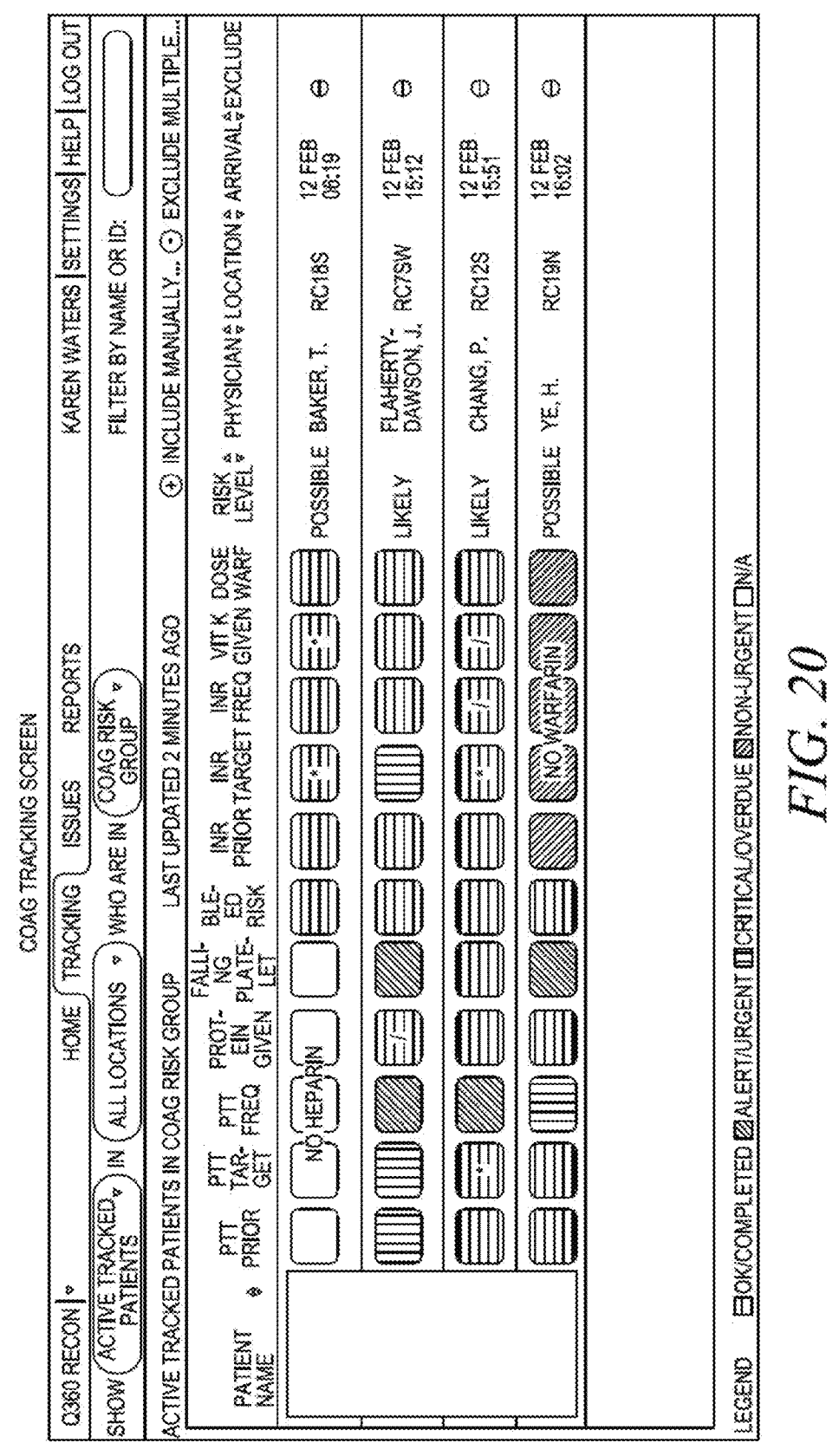

Referring to FIG. 3a, the clinical informatics platform may also comprise a dashboard for a near real-time data processing and predictive clinical surveillance system that identifies high-risk, high-cost patients, tracks necessary care, and supports clinicians to intervene to improve care. The data processing and clinical surveillance tool 302 may be a dashboard for presenting data processing and clinical surveillance and enabling real-time predictive risk tracking Data from disparate data sources 118 are extracted as described herein, normalized and mapped as described herein, then analyzed to obtain clinical tracking data that can be presented by a tool 302 in a graphical user interface of the platform 100. An embodiment of a report is shown in an expanded version in FIG. 3b. A reports tab may enable a user to generate reports related to a number of topics, such as the patient, medical care, and outcomes, and sub-topics, such as demographics, behavioral risk factors, disease risk factors, procedures, therapeutics, utilization, ICU, readmission, mortality, complications, and the like. Since the data are real-time, real-time clinical intervention is enabled as patients who are high-risk and/or high-cost are more readily identifiable and easy to track. The screen in FIG. 3b displays a 'Tracking' tab of the tool 302 that shows active tracked patients in a hospital unit who are in the acute myocardial infarction (AMI) risk group. Demographic information is available for each patient as well as therapeutics over a given time period, risk level, physician, location, arrival date/time, and the like. The tool 302 provides a way to manually include or exclude patients from tracking A reason may need to be recorded for exclusion or inclusion. The reason may be selected from a list of standard reasons or manually entered or entered in some other way. Filters may be applied to the data presentation. In an 'Issues' tab, issues, such as 'all open issues' may be shown for patients being tracked. The 'Issues' tab may show Patient name, Issue, Physician, Location, Due By timer, and the like. Filters may be applied to this display. For example, patients in only certain locations may be included in the listing, or in other embodiments, patients in all locations may be included. In another example, patients in only certain risk groups may be included in the listing, or in other embodiments, patients in all risk groups may be included. When a patient is selected, their profile may be displayed. For example, patient information may be shown, their AMI risk profile may be shown, or some other risk profile may be shown. In an example, the AMI risk profile may include statuses over time, such as location, blood pressure, temperature, anticoagulants, beta blockers, thrombolytics, CK-MB, triglyceride levels, CBC, glucose level, troponin levels, images taken, procedures done, and the like. A patient may be manually excluded or included in a risk group, but a reason may need to be recorded. The reason may be selected from a list of standard reasons or the reason may be manually entered. Given a patient's risk profile which is known in real-time, predictive analytics may be applied to identify patients at risk. Patients at risk may be automatically detected by the tool 302, such as by using the AMI detection algorithm tool shown in FIG. 19. The visual dashboard of the tool 302 provides a number of benefits. The platform 100 enables "at a glance" status checks on the floor, automates and optimizes identification of patients to be tracked, reduces the number of patients to be tracked, connects knowledge to action, provides clinical data for better understanding, compresses "time to intervention" for better outcomes, compresses "time to action" for core measure compliance, reduces cost, morbidity, and mortality, and the like. FIG. 20 depicts another example of a clinical surveillance dashboard for a risk group of patients on anticoagulation medications.

In an embodiment, the clinical surveillance dashboard may enable a health care provider or health practitioner to see each patient's countdown to events that need to be done within a certain period of time, such as within an hour of admission, day of admission, and the like. The health practitioner's plan for care can be viewed by doctor, patient, floor, clinic, disease, and the like, along with all of the relevant data and measures that went into establishing the plan. The plan for care itself may be automatically customized based on an indication, therapeutic protocol, and the like. The plan and/or its timeline for action may be updated in real-time, such as when new data become available to the platform. The plan for care may be for a particular patient and may be adjusted based on real-time data regarding that patient. For example, if the real-time data indicates that the patient is recovering more slowly than expected, the plan may be revised to include higher doses of painkillers and more frequent testing and monitoring.

The clinical informatics platform 100 may also comprise a tool for a near real-time data processing and predictive clinical surveillance system that identifies diabetic patients. Data from various sources, such as laboratory data and pharmacy data, may be analyzed using an algorithm to determine if a patient may be diabetic, based on some known combination of laboratory and pharmacy data that indicates a high likelihood of the pathology.

The clinical informatics platform 100 may also comprise a tool for a near real-time data processing and predictive clinical surveillance system that identifies cohorts of patients that fit the JCAHO guidelines.

The clinical informatics platform 100 may also comprise tools for analytic model building. For example, to build a disease model, aspects of the disease that might be of interest in determining the quality, cost, and/or outcome of care may be obtained from the literature, textbooks or know how. These aspects may be defined as inputs to the model in terms of rules, attributes, characteristics, criteria, or the like. These inputs may be defined in a rules database 112 and updated periodically or as needed. Data may be analyzed according to the model by the platform 100 to enable determining a disease state. For example, a diabetes model may be consulted to determine or predict if a patient has diabetes. The model may require that certain data be available, such as diagnoses codes, glucose test results, HgbA1C levels, outpatient prescriptions, and the like. These data may be analyzed according to rules of the model. For example, the model may indicate that a patient is diabetic if a glucose level is over a prescribed amount and if an HgbA1C level is over a prescribed amount. If the actual glucose level is below the prescribed amount and the HgbA1C level is above the prescribed amount, when these data are input to the model, it may be determined that there is a moderate likelihood that the data corresponds to a patient with diabetes. Other disease specific models may be enabled by the platform 100, such as models for congestive heart failure, hypertension, COPD, dyslipidemia, coronary artery disease, peripheral vascular disease, acute myocardial infarction, cerebrovascular disease, stroke, renal failure, osteoarthritis, rheumatoid arthritis, ulcer, depression, heart failure, pneumonia, septicemia, adult preventative screening, CAD, adult asthma, pediatric asthma, chronic kidney disease, anticoagulation/VTE, fibromyalgia, back pain, obesity, osteoporosis, estrogen-related disorders, inflammatory bowel syndrome, dementia, BPH, pain management, immune disorders, HIV, colon cancer, prostate cancer, breast cancer, pneumonia, TB, anemia, lupus, gout, thyroid disorders, hepatitis, atrial fibrillation, arrhythmias, and the like.

The clinical analytics platform 100 may support application programming interfaces (APIs) integrated with the data warehouse 114 to allow the development of applications that can leverage the normalized data, such as for applications directed to regional healthcare issues, individual health providers, research or clinical studies, pharmaceutical and biotechnology companies, and the like.

The clinical analytics needs of ambulatory providers may be significantly different from those of acute care providers. Care in ambulatory environments may occur over a longer time period with multiple discrete events. These events may occur in different locations, under the care of multiple providers, and prescribed treatments may only show results over an extended period of time. In addition, documentation, coding practices, disease specificity and multiplicity all combine to make clinical analytics far different from similar efforts in hospital settings. The clinical informatics platform is uniquely designed to handle the specific needs of ambulatory care providers. The clinical informatics platform integrates clinical, claims, lab, and other data to generate a complete and longitudinal view of member organizations' patient populations, provides disease-specific clinical classification and advanced analytics to define appropriate patient cohorts, treatment pathways, outcomes and associated costs, provides treatment effectiveness and outcomes analysis to support evidence-based process improvements, thus allowing physician practices to enhance cost-effectiveness while providing the highest quality patient care, facilitates comparative analytics and benchmarking by aggregating data from participating medical groups, facilities, practices, and physicians into a single, standard clinical ontology, supports organizations to develop, compare, and share best practices and performance improvement strategies through our unique collaborative programs, and the like. The clinical informatics platform may enable users to access comprehensive patient data and the data necessary for quality reporting, effectively manage chronic disease patients with protocol tracking tools and task lists, automate real-time surveillance and employ clinical decision support at the point of care with real-time reminders and alerts, and the like. The clinical informatics platform may help organizations demonstrate the value of the care they deliver, receive appropriate compensation for the quality of the care they deliver, get clinical detail on best practices that lead to improved outcomes, improve patient care in a timely manner by combining real-time clinical surveillance with robust retrospective clinical analytics, attract patients by enhancing their organization's reputation for quality, and the like.

The clinical informatics platform may also enable the activities of life science firms. Using the clinical informatics platform, life sciences firms may be able to quantify patient populations, market share, and market opportunities, all by disease severity and co-morbidities. The clinical informatics platform may profile patient segments with detailed clinical specificity (e.g. lab results and radiology reports), identify treatment decisions by physician specialty and practice setting, and elucidate the associated costs and outcomes—information vital to generating appropriate and tailored marketing strategies and tactics.

The clinical informatics platform may provide life sciences companies with the tools necessary to understand the clinical drivers of treatment decision-making, to quantify their brand's unique benefits, and to accurately assess a myriad of market opportunities. The clinical informatics platform may offer the timeliest and most complete clinical data needed to manage and succeed in today's challenging marketplace. The clinical informatics platform's longitudinal clinical data offer unprecedented insight into brand choices and the associated clinical outcomes and cost effectiveness. With the clinical informatics platform, life sciences firms can more accurately and expediently quantify patient populations, market share, and market opportunities. The clinical informatics platform enables profiling patient segments with detailed clinical specificity (e.g., lab results, radiology, co-morbidities), identifying the clinical drivers of treatment decisions by physician specialty, and elucidating the costs and outcomes associated with treatments. The clinical informatics platform may provides longitudinal clinical data needed to gain a more accurate picture of specific patient sub-populations, brand-specific clinical profiles, including lab and radiology results, for improved marketing message development and effectiveness tracking, clinical evidence for the development of refined segmentation strategies, clinical data highlighting which treatments occurred when, and by which specialty, to accurately define the sequence of care and associated outcomes, and the like. The clinical informatics platform clinical data enables life sciences companies to: measure clinical outcomes within specific patient segments, more accurately identify unmet needs and associated market opportunities, tailor marketing messages to accurately address the specific needs of provider groups and patient cohorts, and the like. The clinical informatics platform enables users to quickly and accurately answer numerous questions, such as the following: Am I attracting the right patient segments based on my product's unique clinical profile?; How does the clinical profile of patients on my brand compare to those of my competitors, both branded and generic?; In which patient segments does my brand outperform the competition in terms of clinical outcomes and cost effectiveness?; How do I maximize the pricing and reimbursement for my brand?; and the like.

The clinical analytics platform 100 may be deployed in many different environments to provide for data extraction, processing, storage, analysis, and presentation. For example, the platform 100 may be deployed in ambulatory care facilities, life science firms, acute care facilities, hospice, clinical trial facilities, insurance companies, senior living facilities, veterinary facilities, epidemiological centers, triage centers, emergency rooms, and the like.

The clinical informatics platform may further be used for social network analysis of health care providers, provider network shared patients, referrals and the like. By way of one example, in instances where such analysis is desired, the clinical informatics platform may extract various data from numerous health care providers that relate to patient movement and treatment within the network. The clinical informatics platform can then normalize the data and apply analytics to the data that will display patient movement, course of treatment and progress, physician referral, or other results based on the data provided and information desired. The network in question and its associated data may be visualized and integrated into the clinical informatics platform user interface through the use of a network analysis visualization tool.

Further, the clinical informatics platform may enable social network analysis of health care provider, such as primary care physicians and specialists, interactions which may enable managing provider networks and provider network shared patients or referrals. The social network analysis results may be visualized on a coordinate system, such as an x-y coordinate system, an xyz coordinate, a pie chart, a radar display, a GIS map, other non-xy plots, and the like. For example, the Y component of the coordinate system may be the physician and the X component may be key care variables around the way that care is delivered in a particular disease. Another coordinate may identify the physicians by their clinic. The visualization may be examined for physicians who cluster together by using an algorithm. The clusters may be indicative of patterns of care that are characteristic of the cluster, and may be suggestive of a pattern of care, cost, or outcome that is either positive or negative.

Social network analysis for managing provider networks and provider network shared patients or referrals may be described with reference to an example involving an internist or specialist network. A first step in social network analysis in this example may involve identifying all of the encounters between a physician, a patient and a medical center to create a bi-partite network. For example, connections between physicians, patient and physician, and another physician may be represented in the network. The bi-partite network may then be condensed into a doctor-to-doctor network. The doctor-to-doctor network may be made bi-partite again in that all of the same doctor type to same doctor type connections may be eliminated. The now condensed network may be an internist to specialist network.

A social network analysis visualization tool may enable visualizing a network in many ways, such as by using a coordinate system. For example, groups of providers may be differentiated by a specific color, a specific shape, or a size. The thickness of the connections, represented as lines, between members of the group may be a measure of how many patients they share between them. This measurement may be utilized as a weight in the analysis. From this visualization, significant patterns may become apparent that may enable examination of characteristics of the practice of medicine. For example, the social network analysis visualization may be used to show patients who are on MEDICARE versus commercial insurance versus government insurance. The analysis visualization may identify patient encounters for patients that are above average. The analysis visualization may show a practice cluster that stands out in their utilization of imaging, patient outcomes, cost, and the like by being able to correlate the clusters and connections with various metrics. For example, the analysis may enable a mapping of the quality and cost of a network of doctors. In some embodiments, the size of the objects representing a group may be a visual indicator of some kind of measurement, such as how much was spent per visit on a patient. In this embodiment, the social network visualization may show that some groups practice the same medicine and get different outcomes at the same cost.

The social network analysis visualization tool may enable determining who are popular providers and influencers of other providers and care outcomes, not by examining communication or information flow, but rather by analyzing actual care characteristics.

Figure 14:
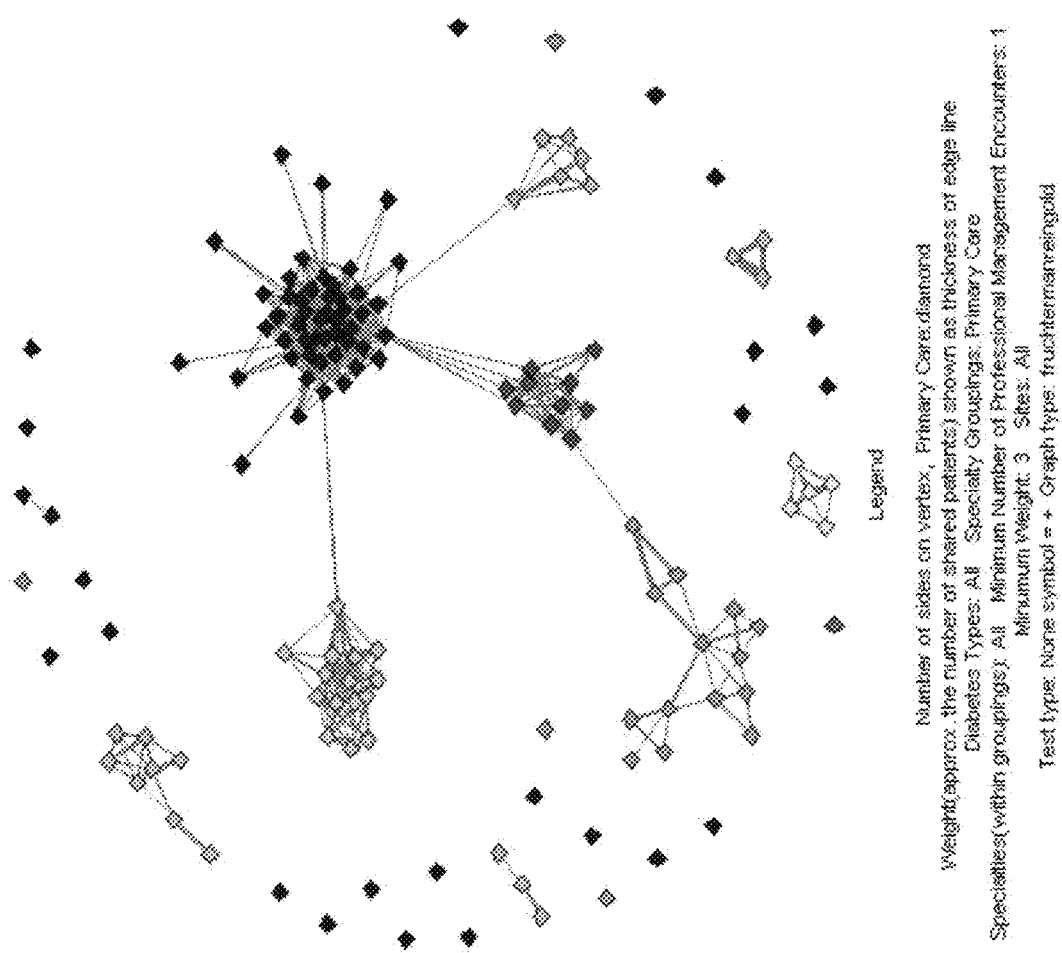
FIG. 14 shows a visual representation of interactions in a primary care physician network.

Referring to FIG. 14, a visual representation of interactions in a primary care physician network is shown. Each diamond represents a primary care physician in the network, or a vertex, and each connecting line between each primary care physician, or the edge between two vertices, represents the number of shared patients by the thickness of the line. The visualization shows distinct clusters of physicians who have many shared patients among them with a smattering of smaller clusters and physicians who do not share patients with any other physicians or have very few shared patients. In this example, primary care physicians may be identified as part of an institution or practice by a unique shading or coloring of the diamond.

Figure 15:
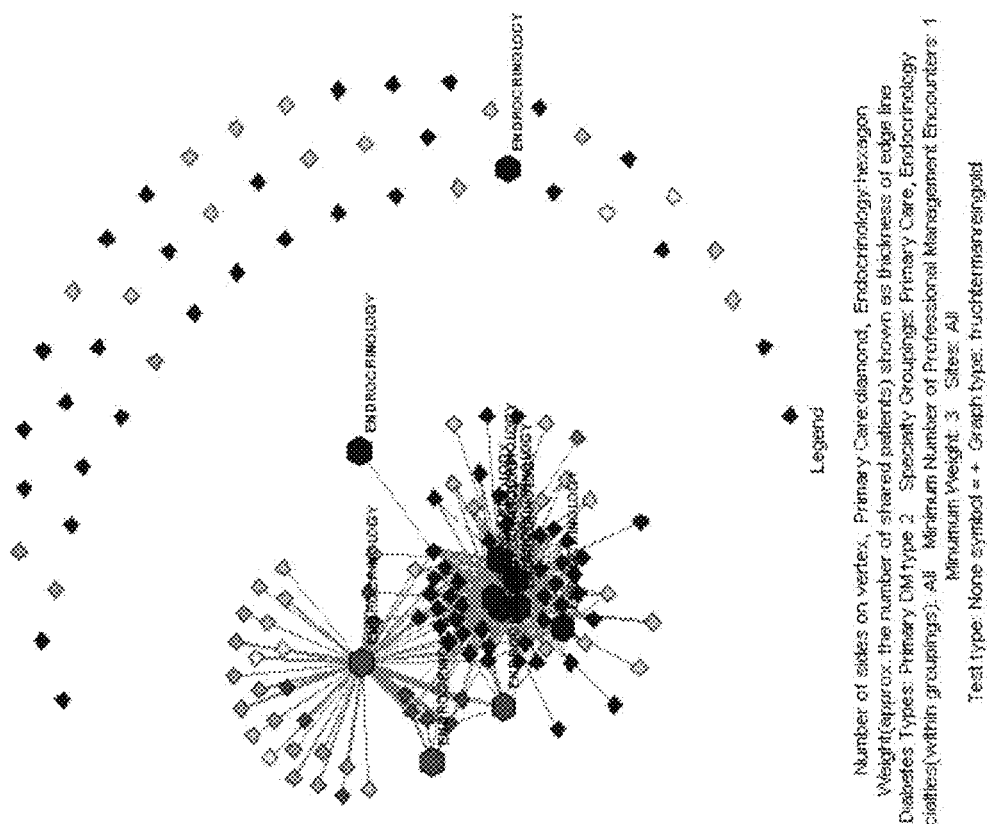
FIG. 15 shows a visual representation of interactions among primary care physicians and endocrine specialists in a referral network.
Figure 16:
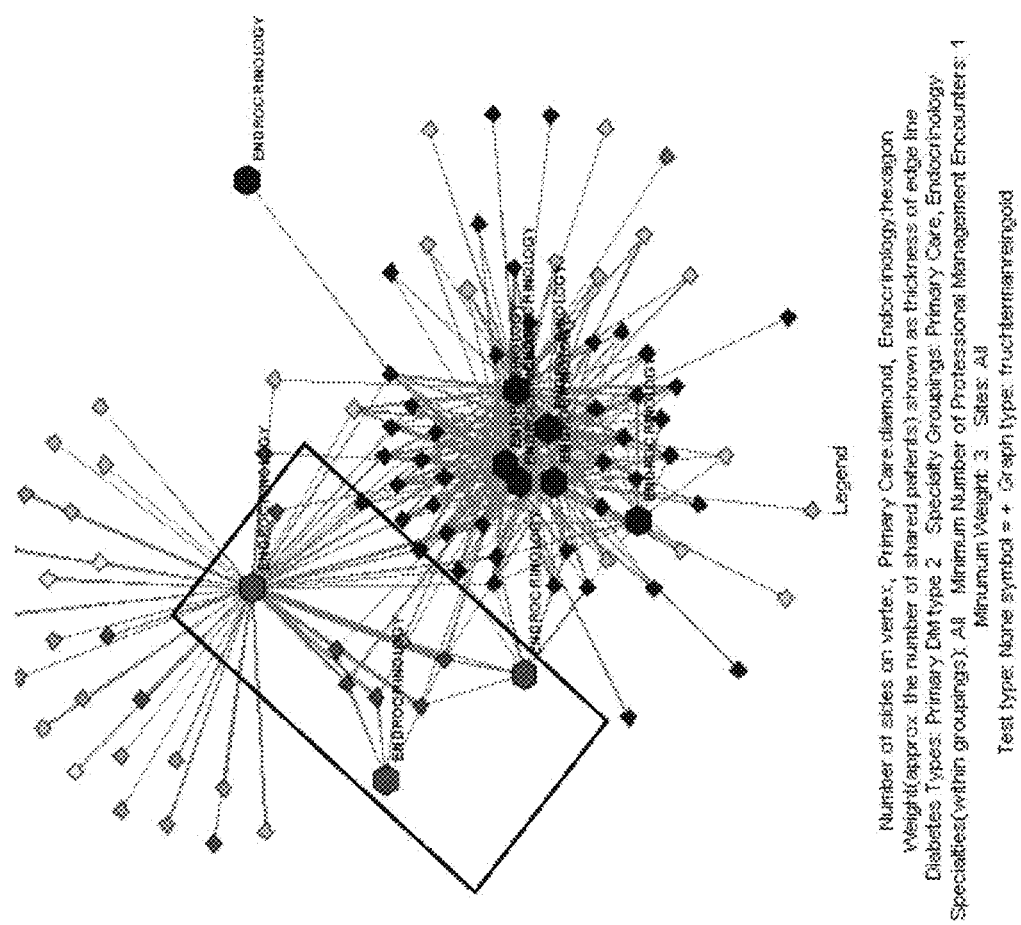
FIG. 16 shows another visual representation of interactions among primary care physicians and endocrine specialists in a referral network.

Referring to FIGS. 15 and 16, an example of a social network analysis of interactions among primary care physicians and specialists in a referral network is shown. In this example, a visual representation of a social network analysis of interactions among primary care physicians and endocrine specialists for diabetes mellitus type 2 in a referral network is shown. FIG. 16 is a close-up view of the referral network in FIG. 15 where the isolated physicians and endocrinology specialists have been removed for clarity. Each diamond represents a primary care physician in the network, or a first vertex, each hexagon represents an endocrinology specialist, or a second vertex, and each connecting line between each primary care physician and endocrinology specialist, or the edge between two vertices, represents the number of shared patients by the thickness of the line. In this example, primary care physicians may be identified as part of an institution or practice by a unique shading or coloring of the diamond. The visualization shows a distinct cluster of physicians and an endocrinology specialist, where a single endocrinology specialist receives many shared patients or referrals. The visualization also shows physician or endocrinology specialist clusters where multiple specialists are referred to by the physicians. Finally, there are also physicians displayed who make no referrals, as well as endocrinology specialists who receive few or no shared patients or referrals. The visualization highlights where certain line thicknesses could be increased, that is, where more shared patients or referrals can be made between physician and endocrinology specialist. The visualization also enables correlating metrics, such as expense, care outcomes, compliance, and the like, with a thickness of connection. By identifying endocrinology specialists by referral, the visualization may suggest which specialists to go to and which ones to avoid. In embodiments, the social network analysis may be very sensitive for a particular institution. For example, the visualization shows that certain endocrinology specialists are members of distinct clusters, where the distinct clusters are representative of referral networks arising from distinct institutions. In this example, the three endocrinology specialists within the rectangle on FIG. 16 are all part of the same clinic but the top-most specialist seems to be a major part of two clusters in the referral network, while the two other endocrinology specialists get few shared patients or referrals from physicians in the other cluster. Thus, the visualization may identify certain practitioners who are key to the interactions in the referral network or certain practitioners who are draining referral patients from a certain clinic. The visualization may be examined over time to determine the ebb and flow of the referral network. As clusters and connections become apparent, they may be actionable, and modifications may be made to practices.

Figure 17:
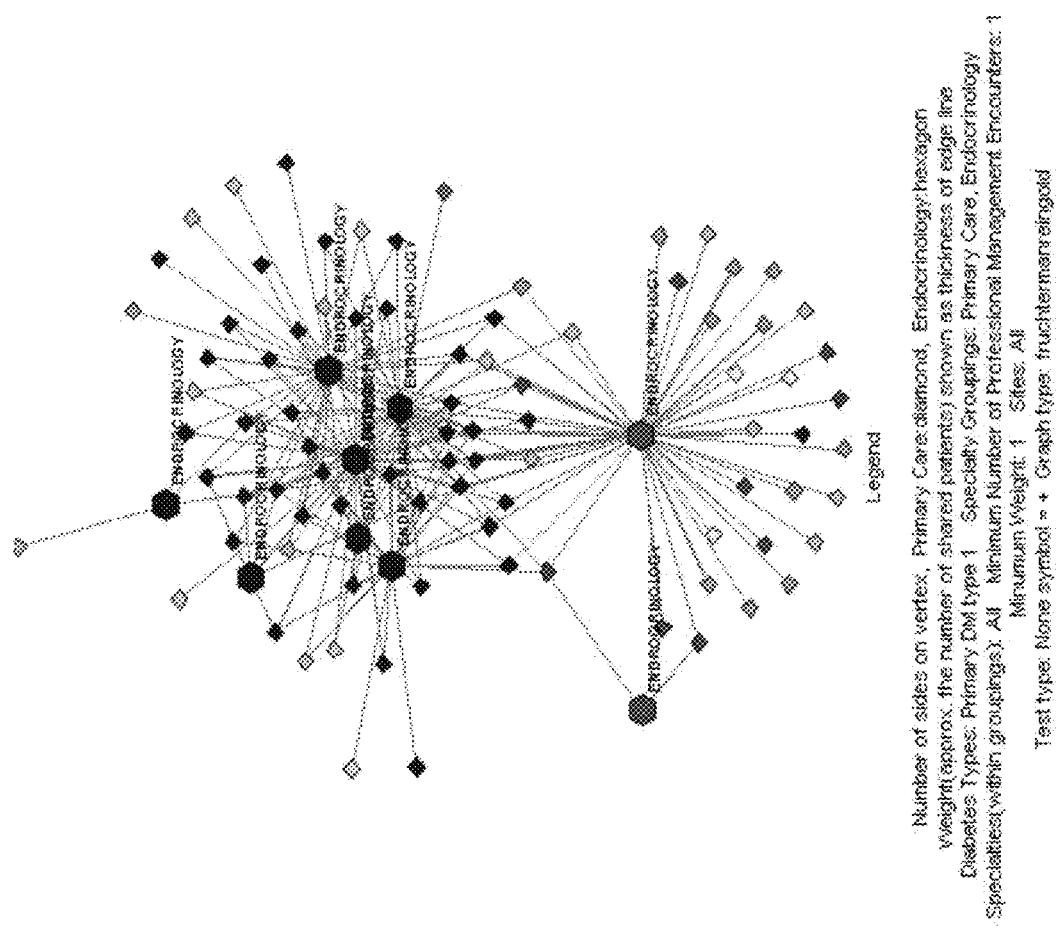
FIG. 17 shows a visual representation of primary care and endocrine care providers in a referral network.

Referring to FIG. 17, a visual representation of primary care and endocrine care providers in a referral network in diabetes mellitus type 1 is shown. This visualization is different from that shown in FIGS. 15 and 16 in that the disease is different, diabetes mellitus type 1 is an autoimmune disease while diabetes mellitus type 2 is a disorder that is characterized by high blood glucose in the context of insulin resistance and relative insulin deficiency. By examining the differences in the visualizations, a comparison can be made with respect to how care is delivered in a particular disease. For example, in this visualization, there are no isolated primary care physicians, suggesting that primary care physicians will usually refer their diabetes mellitus type 1 patients to a specialist for care.

Figure 18:
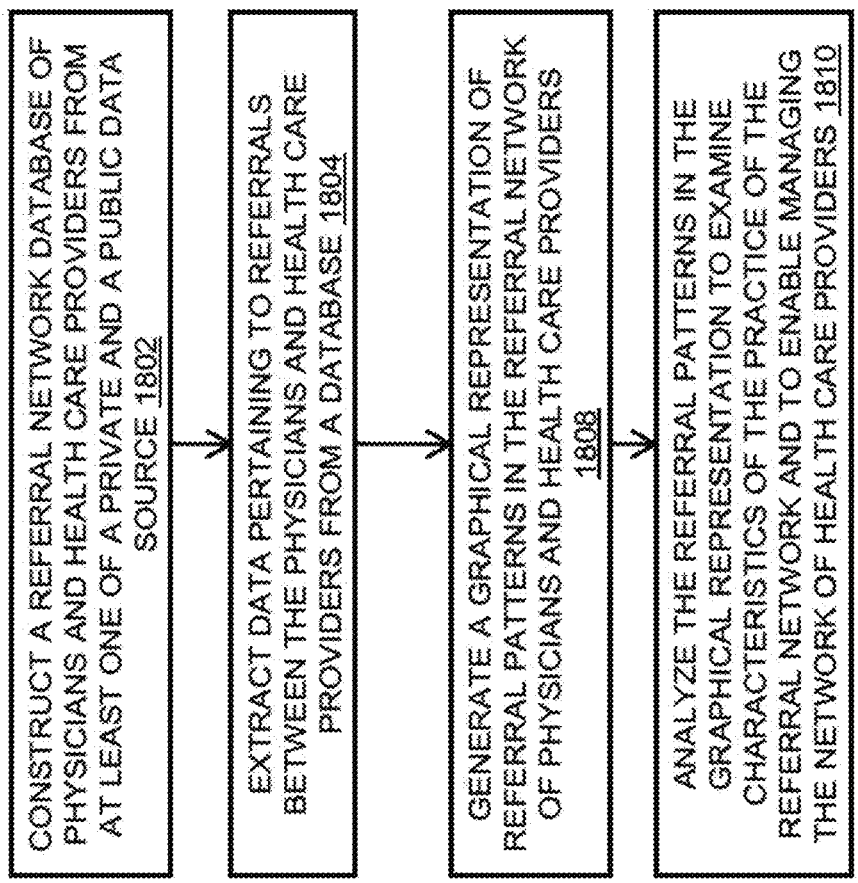
FIG. 18 depicts a logical flow for a computer-implemented method of managing health care providers in a referral network.

Referring to FIG. 18, a method for describing, evaluating, understanding, or managing a network of health care providers may include constructing a referral network database of physicians and health care providers from at least one of a private and a public data source 1802, extracting data pertaining to shared patients or referrals between the physicians and health care providers from a database 1804, and generating a graphical representation of referral patterns in the referral network of physicians and health care providers 1808, wherein at least one element of the graphical representation depicts a measure of an extent of a type of activity within the referral network. The element of the graphical representation may use at least one of size, thickness, color and pattern to depict a type of activity. The element of the graphical representation may depict how many patients are shared among at least two health care providers. The medium may further comprise analyzing the referral patterns in the graphical representation to examine characteristics of the practice of the network and to enable describing, evaluating, understanding, or managing the network of health care providers 1810. The step of constructing a referral network of physicians and health care providers may use data mining techniques to find relationship data between physicians and health care providers. The step of constructing a referral network of physicians and health care providers may identify physicians and health care providers as nodes with linkages in a referral network. The data sources may include automated collection and user-generated data sources for referral network construction. The user-generated data may be from a survey. The data pertaining to shared patients or referrals may be extracted from a claims or electronic health record database. The graphical representation may be an x-y coordinate system. Groups of physicians and health care providers may be differentiated in the graphical representation by at least one of a color, a shape, a shading, a size and the like. The size of the object representing the physicians or health care providers in the graphical representation may correlate with a metric. The metric may be at least one of cost, quality of care, compliance, or other measure of medical care, cost, resource use, quality, patient outcome and the like. In another embodiment, analytical and visual tools may be used to examine the process of care. One such tool may be based on heat maps, which may be a graphical representation of data where the values taken by a variable in a two-dimensional map are represented as colors. Generating a heat map may include taking a sequence of numeric values and representing them with color.

Heat maps may enable identifying similarities in clinics or other groups of doctors in how they manage disease and generally provide care. Heat maps may enable visualizing the organization of healthcare providers into groups based on a similarity in providing care. In this way, healthcare providers may be identified as outliers or who may fit into similar groups. The heat map enables understanding the nature of a group of healthcare providers and enables exploring the characteristics of that group.

Figure 4:
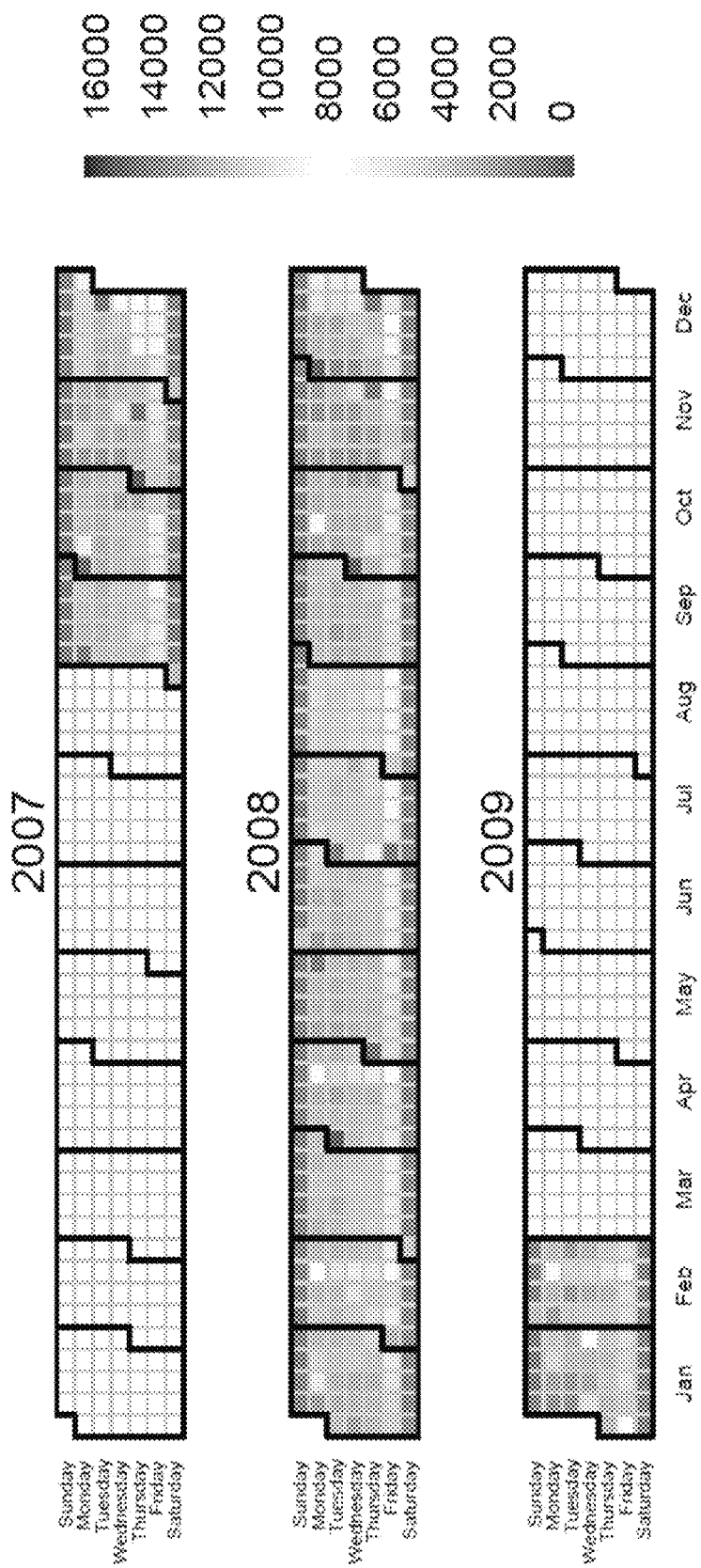
FIG. 4 depicts a heat map of a daily encounter volume.
Figure 5:
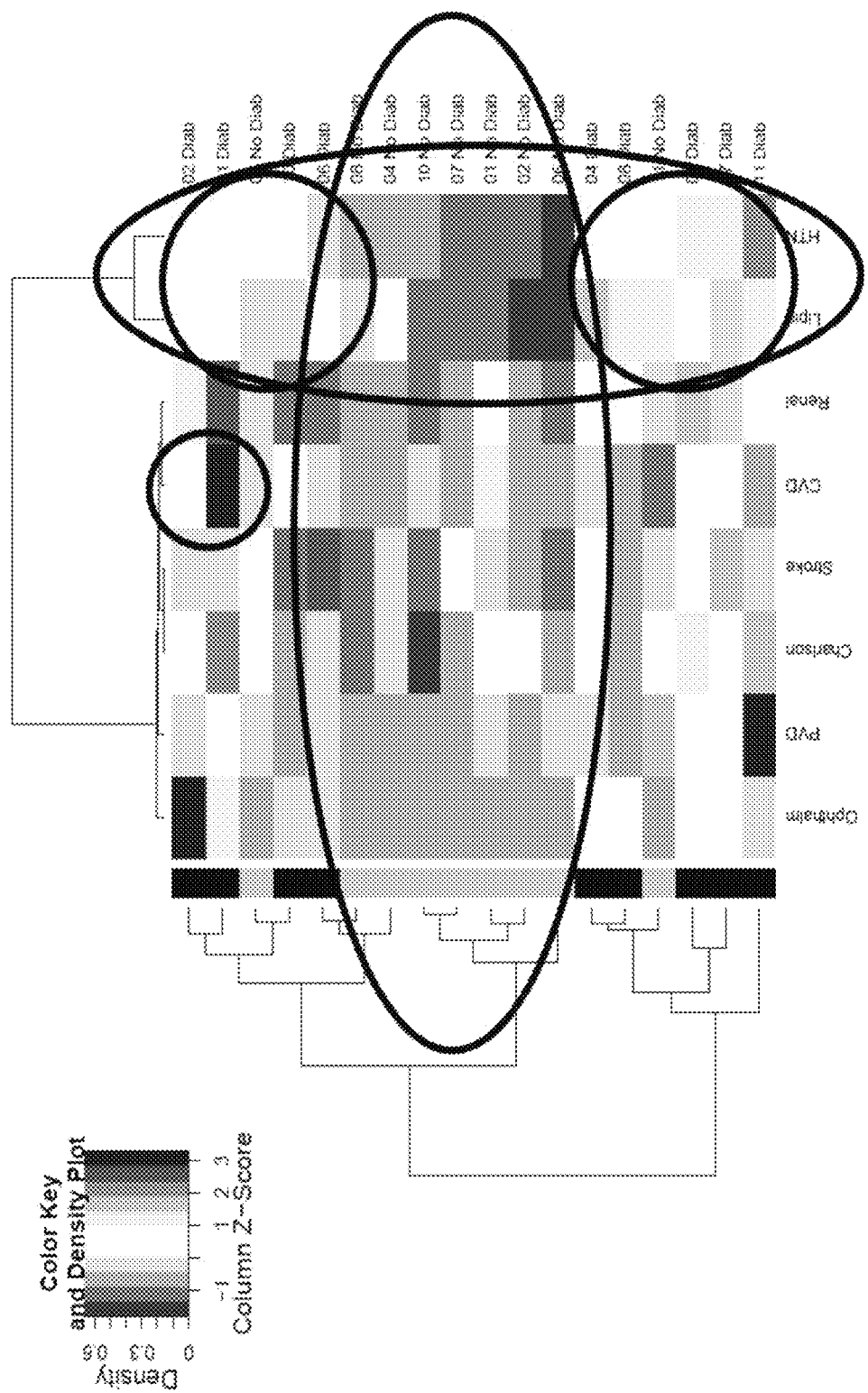
FIG. 5 depicts a heat map of diabetes co-morbidity.
Figure 6:
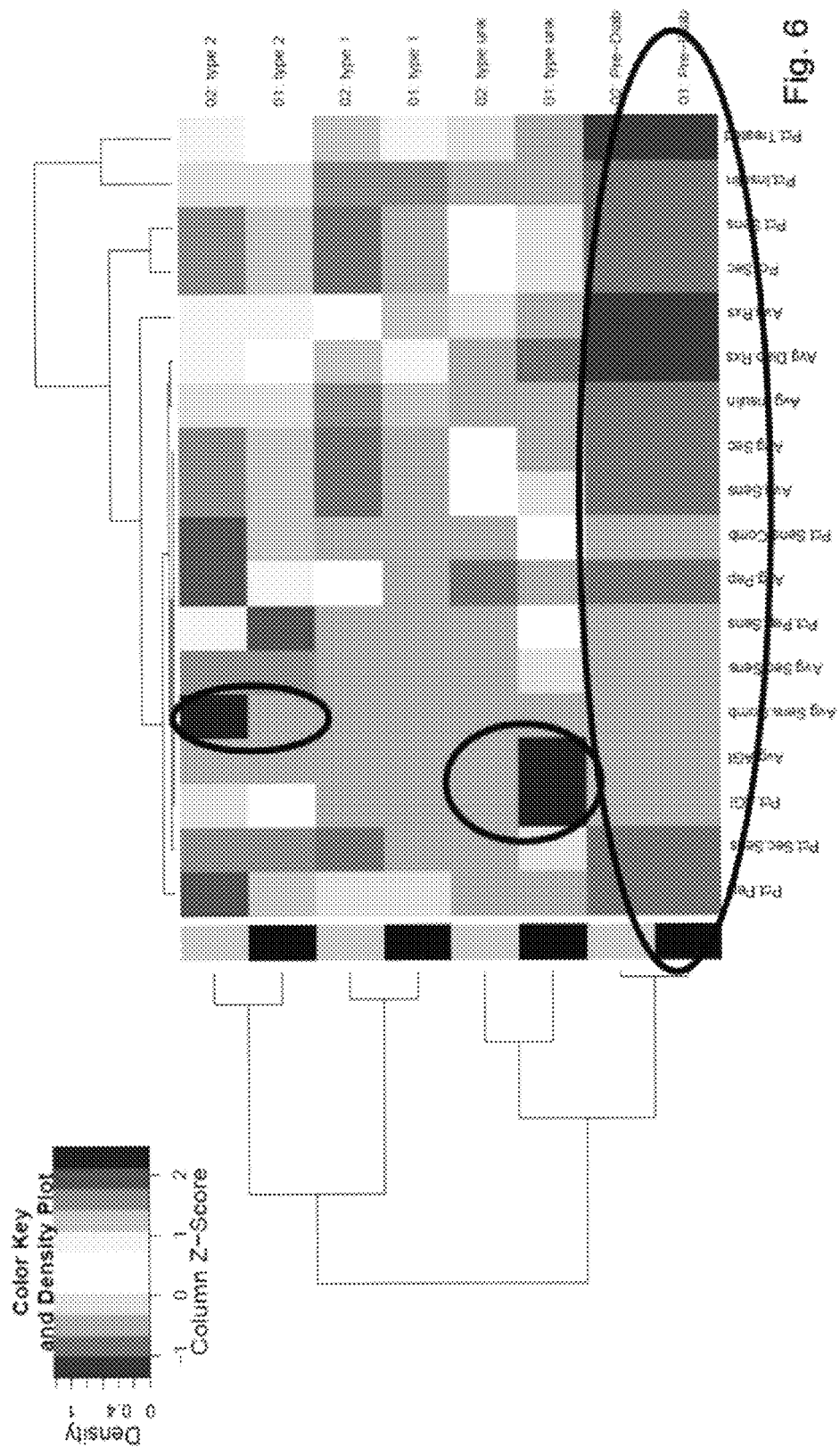
FIG. 6 depicts a heat map for diabetes prescribing patterns.

Heat maps may be used to look to examine various elements of care, such as co-morbidity, prescription use, and the like. For example, referring to FIG. 4, a heat map for Daily Encounter Volume may include taking a sequence of numeric values associated with daily encounters indexed by date, and representing them as a calendar with the days filled with colors representing the values. In another example, referring to FIG. 5, co-morbidities with diabetes are represented graphically as a heat map. One axis of the map relates to diabetic status and the other axis of the map relates to other diseases or conditions, such as ophthalmic disorders, PVD, Charlson co-morbidity score, stroke, CVD, renal disease, lipids, HTN, and the like. The colors of the plot may indicate the presence of a co-morbidity, and in some embodiments, quantify the co-morbidity. In another example, referring to FIG. 6, a heat map for diabetes prescribing patterns is shown. One axis of the map relates to diabetic status and the other axis of the map relates to prescribing patterns, such as percentage of patients treated with alpha-glucosidase inhibitors, percent treated with insulin, percent treated with insulin secretagogues, percent treated with insulin sensitizers, average treatment values thereof, combinations thereof, and the like. The colors of the plot visually indicate the quantifiable differences in prescribing for different diabetic statuses.

Figure 7:
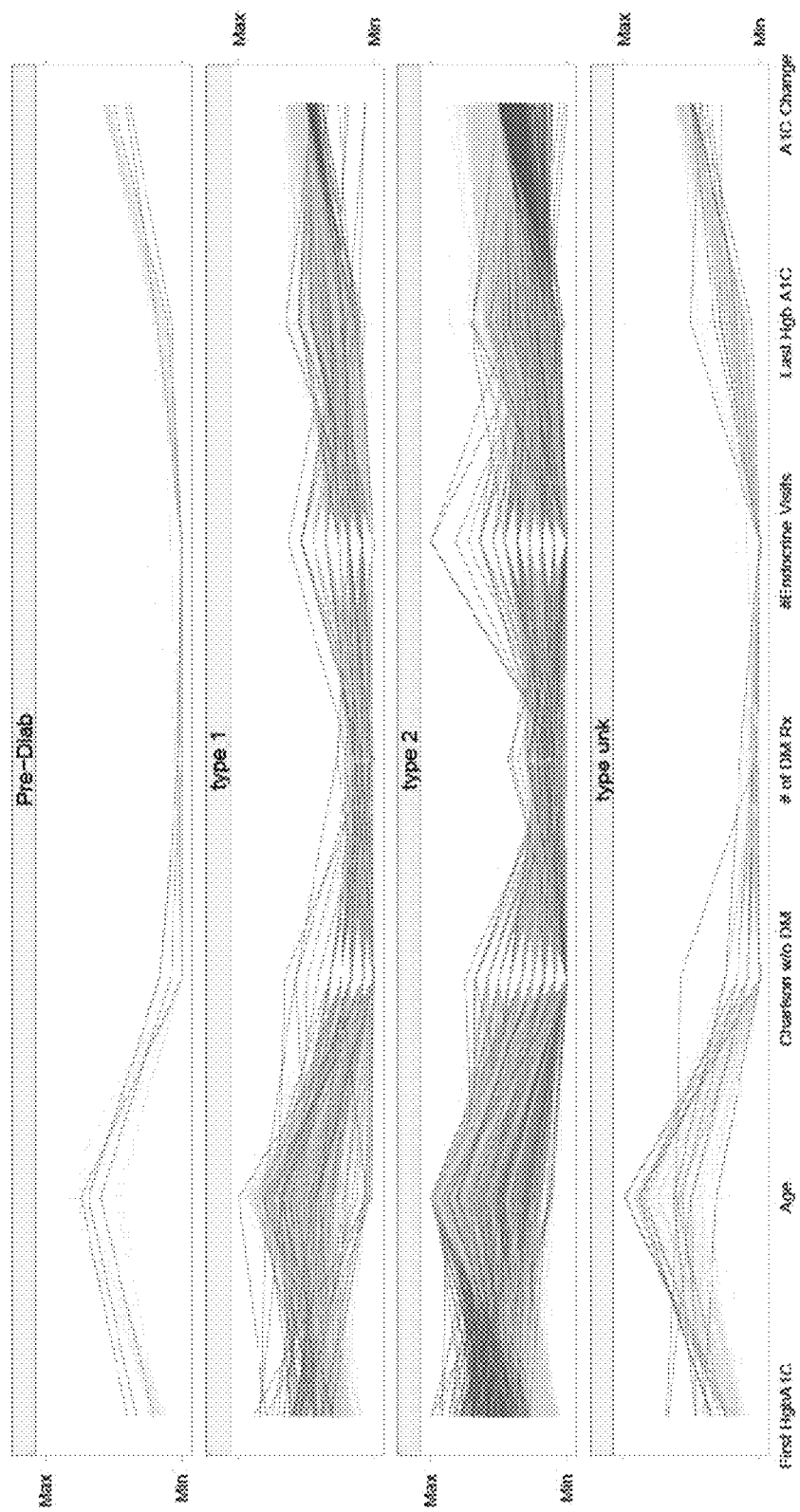
FIG. 7 depicts a parallel coordinate plot of patients with a decrease of >1% in Hemoglobin A1c.
Figure 8:
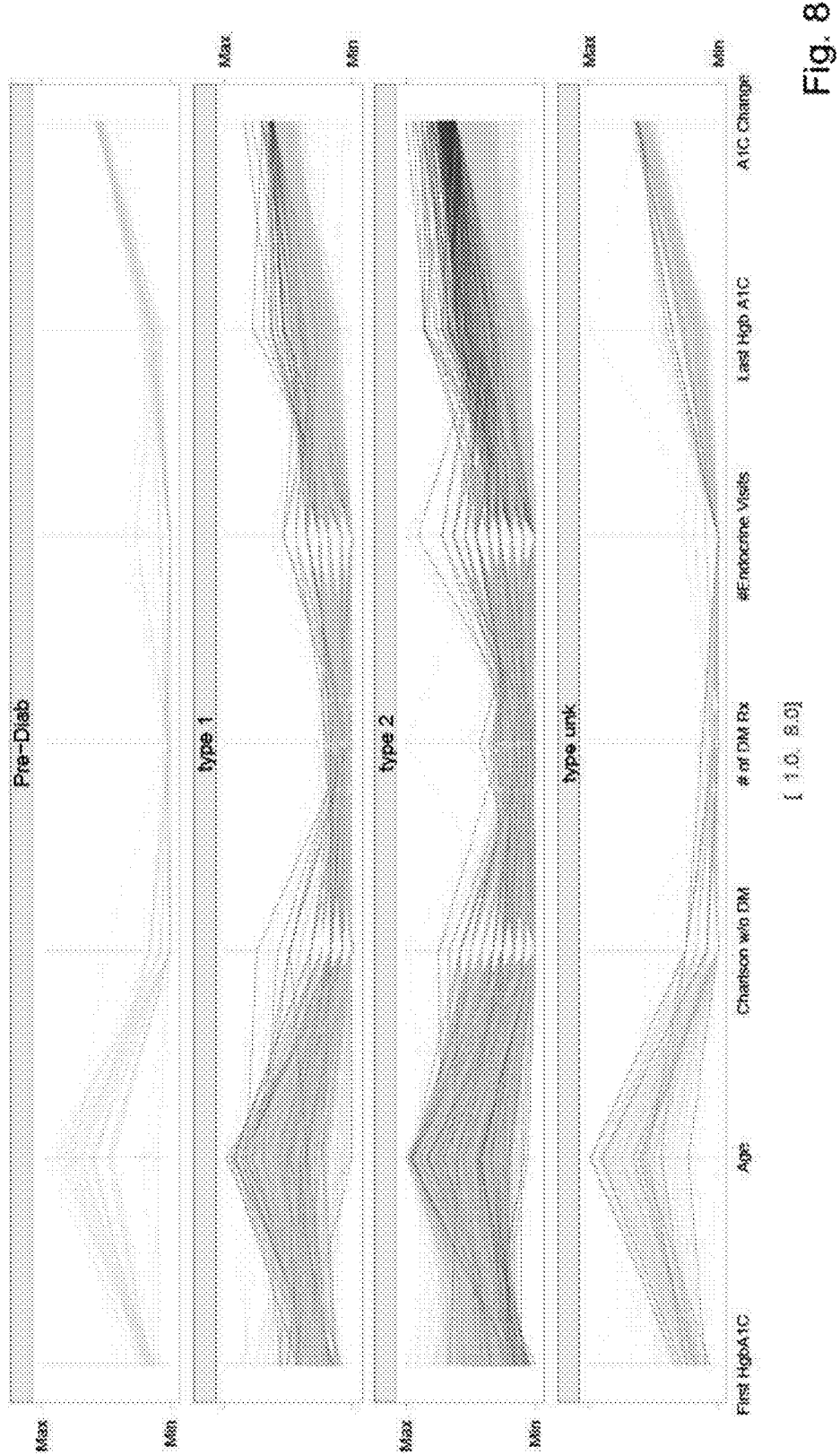
FIG. 8 depicts a parallel coordinate plot of patients with an increase of ≥1% in Hemoglobin A1c.
Figure 9:
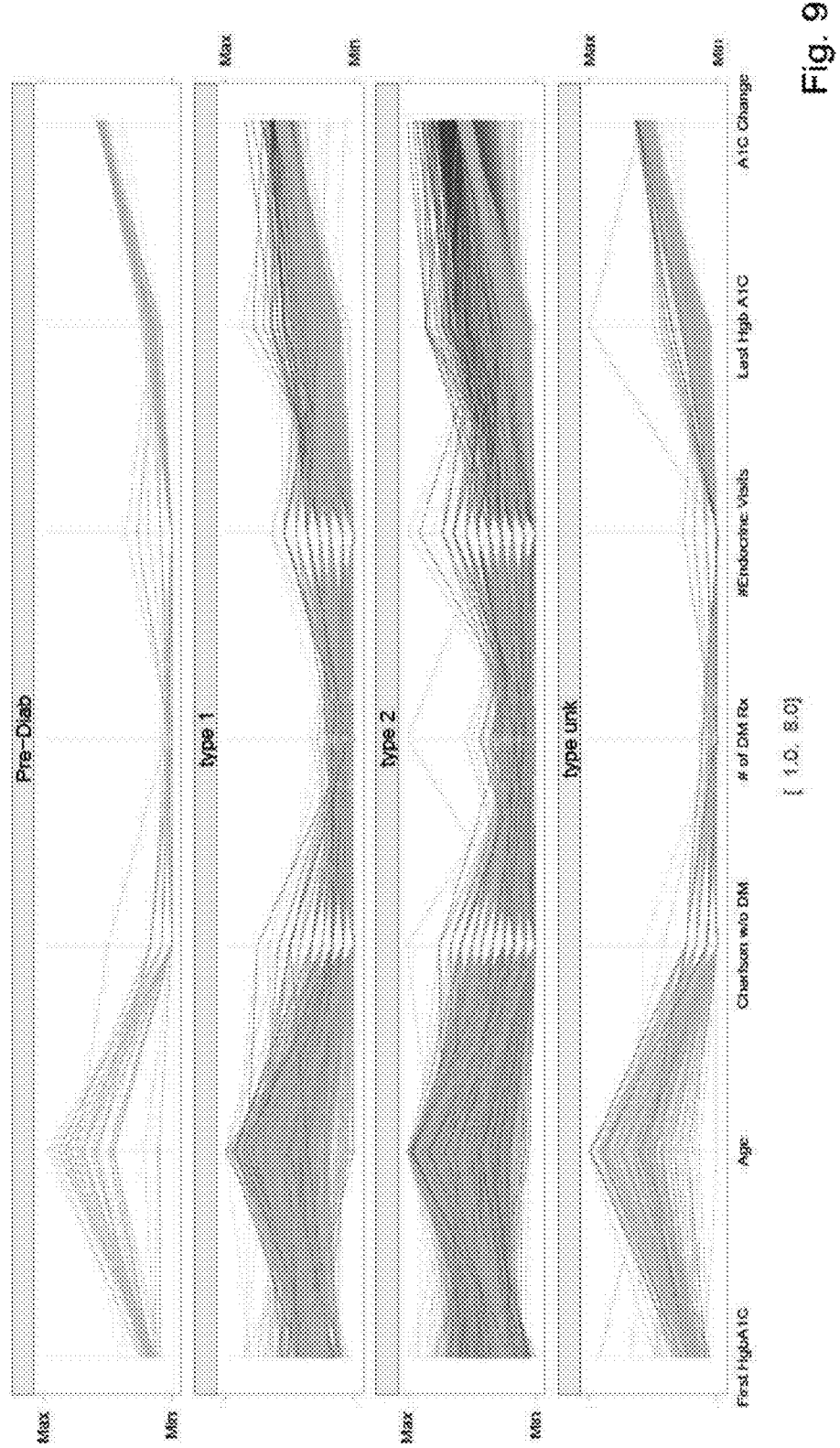
FIG. 9 depicts a parallel coordinate plot profiling change in Hemoglobin A1c.
Figure 10:
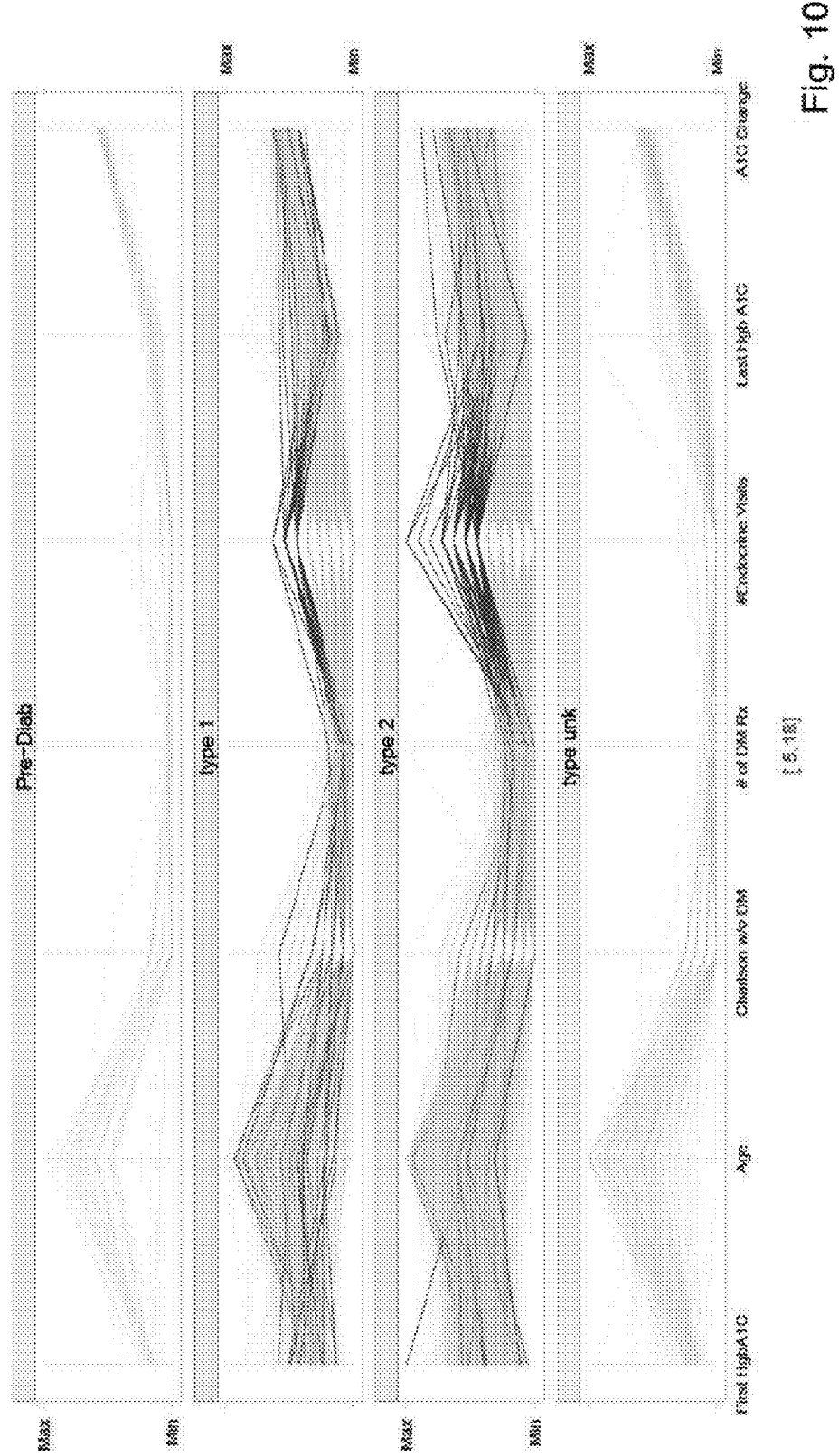
FIG. 10 depicts only those patients who had greater than or equal to five endocrinology encounters on a parallel coordinate plot.
Figure 11:
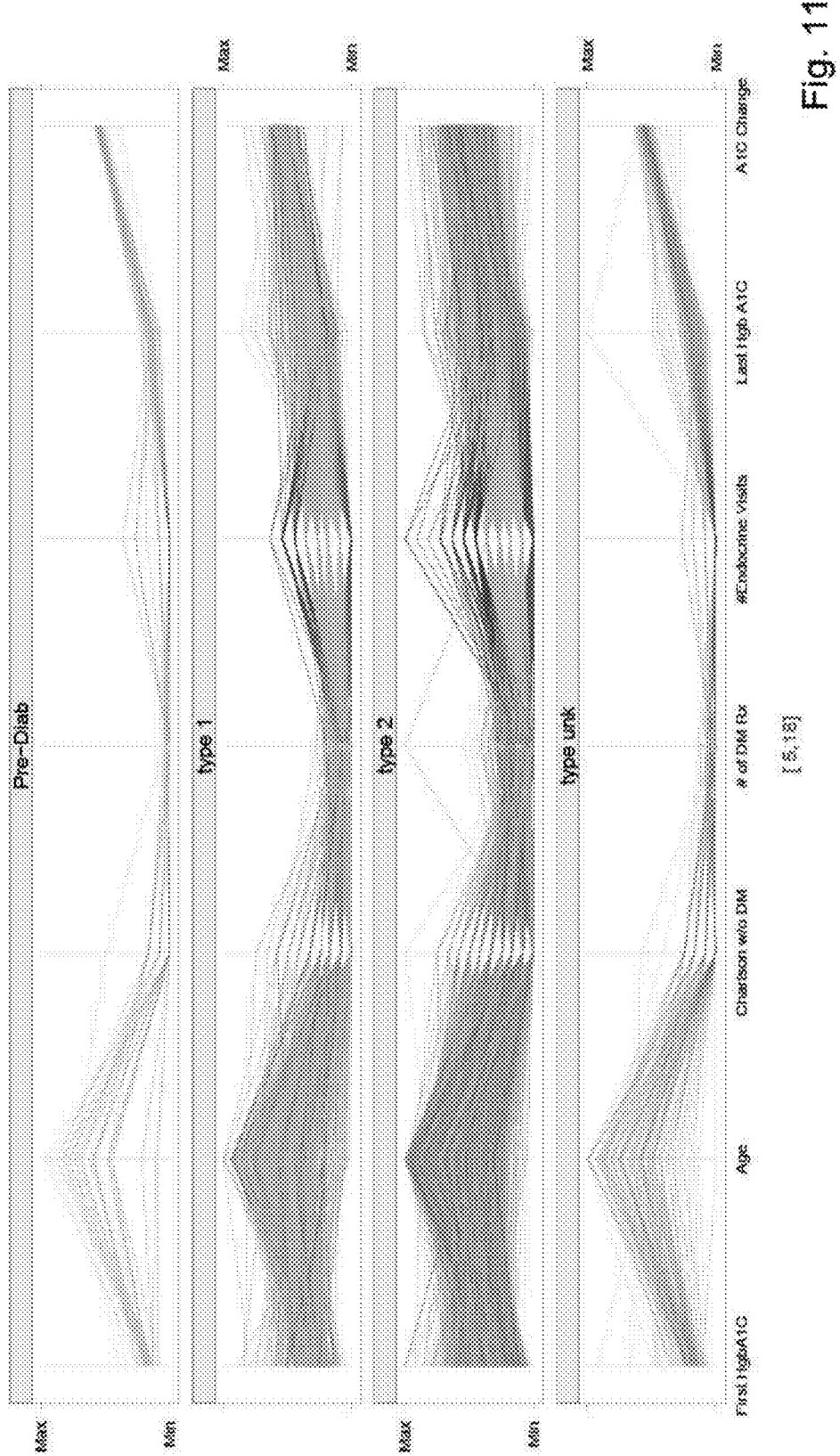
FIG. 11 depicts those patients who had an endocrinology encounter on a parallel coordinate plot.

Another analytical and visual tool that may be used to examine the process of care may be parallel coordinate plots. Parallel coordinate plots are a unique way to look at patterns over time, such as by week, month, year, and the like. Parallel coordinate plots may be used to examine the process of care for individuals in a patient-by-patient way. Each line of the plot may represent an individual patient. For example, referring to FIG. 7, patients, segmented into patients who are pre-diabetic, type I, type II, and type unknown, with a decrease of >1% in Hemoglobin A1c are shown in a parallel coordinate plot where each line represents an individual patient. Levels of hemoglobin A1c are typically used as indicators of diabetes disease management. HbA1c levels depend on the blood glucose concentration. That is, the higher the glucose concentration in blood, the higher the level of HbA1c. Levels of HbA1c are not influenced by daily fluctuations in the blood glucose concentration but reflect the average glucose levels over the prior six to eight weeks. Therefore, HbA1c is a useful indicator of how well the blood glucose level has been controlled in the recent past and may be used to monitor the effects of diet, exercise, and drug therapy on blood glucose in diabetic patients. For example, hemoglobin A1c (HbA1c) levels may be measured at the diagnosis and then measured again after a period of treatment time to determine a change in hemoglobin A1c with treatment. Along with these data points, other elements of care can also be examined, such as number of endocrine visits, number of therapies used, co-morbidity of ages, and the like. In the parallel coordinate plot, a pattern may emerge of people who do well and people who don't do well with respect to their care map. Referring to FIG. 8, patients with an increase of ≥1% in Hemoglobin A1c are shown in a parallel coordinate plot where each line represents an individual patient. Referring to FIG. 9, a parallel coordinate plot profiling change in HbA1c is shown. Referring to FIG. 10, only those patients who had greater than or equal to five endocrinology encounters are shown on the plot. Referring to FIG. 11, those patients who had an endocrinology encounter are shown on the plot.

Figure 12:
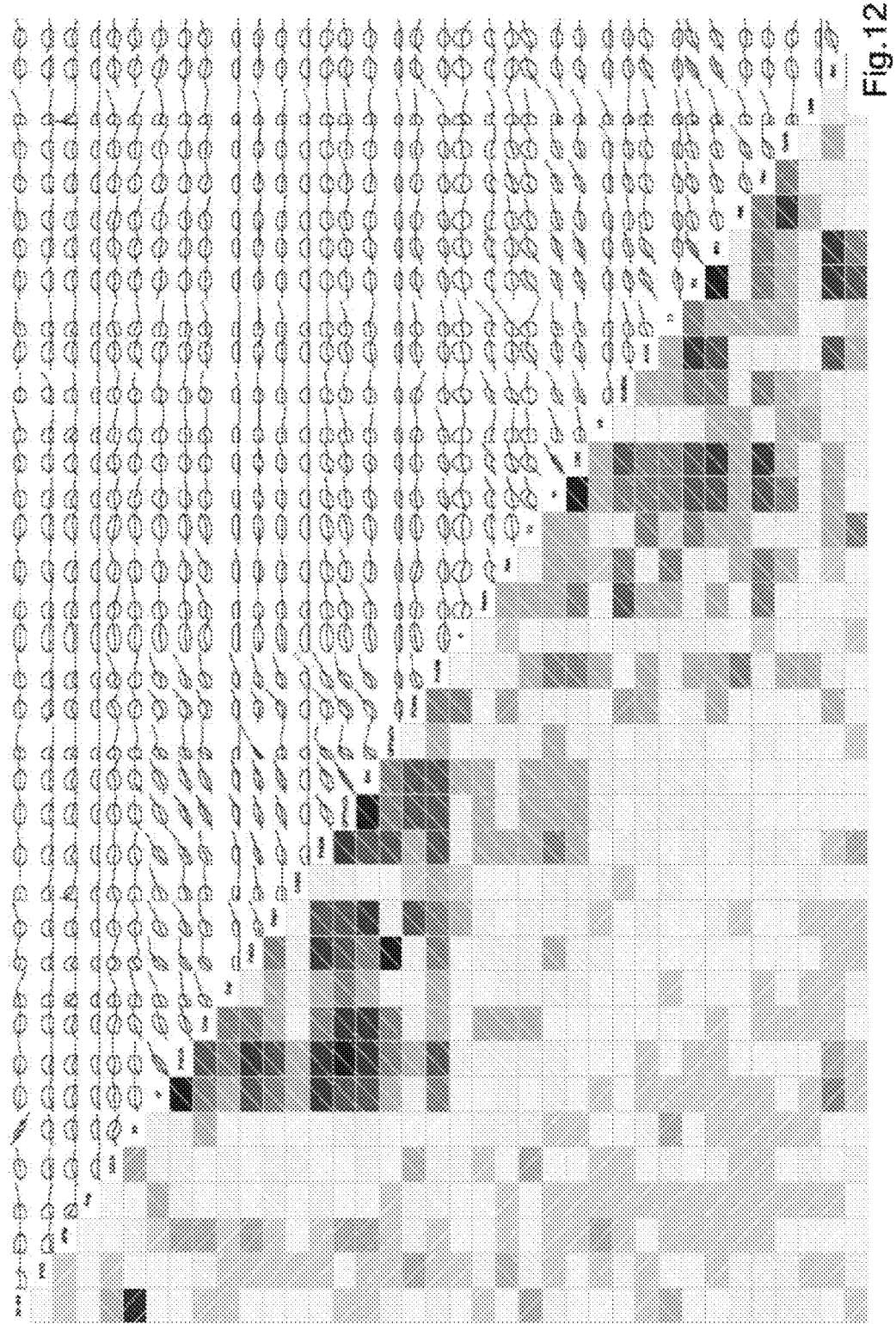
FIG. 12 depicts a plot of physicians treating diabetes by outcome and resource utilization.

Referring to FIG. 12, a corrgram plot of physicians treating diabetes by outcome and resource utilization is shown. Each column and row represents a particular characteristic of clinical practice in the care of diabetes such as percent patients with renal failure, on insulin, with high LDL, and having type 1 diabetes, so that each characteristic is represented once vertically, and once horizontally. The ordering of the placement of each characteristic on the chart is determined by a statistical determination of the correlation of each characteristic with the others in an analysis of many different physician practices. Highly correlated characteristics will be clustered together horizontally and vertically using a defined algorithm. The intensity of the correlation is indicated by the color of the boxes on the lower left half of the corrgram at the intersection of each horizontal and vertical characteristic, with dark blue being most highly positively correlated, and dark red being most negatively correlated. The white lines within the boxes are a visual aid to demonstrate the direction of correlation, and help identify outlier boxes. The matrix in the upper right adds additional information about the correlation, showing an ellipse encompassing 68% of the most concentrated data points from each practice, and a line indicating a loess smoothed curve of the data points from each practice. The corrgram can help to identify which care parameters are correlated with each other in the practices of physicians treating patients with diabetes. For example, this corrgram demonstrates that the percentage of patients in a practice who have a hospital admission is highly correlated with the average amount of inpatient charges for this practice. Also, the percentage of a practice over the age of 65 is negatively correlated with the percentage who have high LDL laboratory values.

Figure 13:
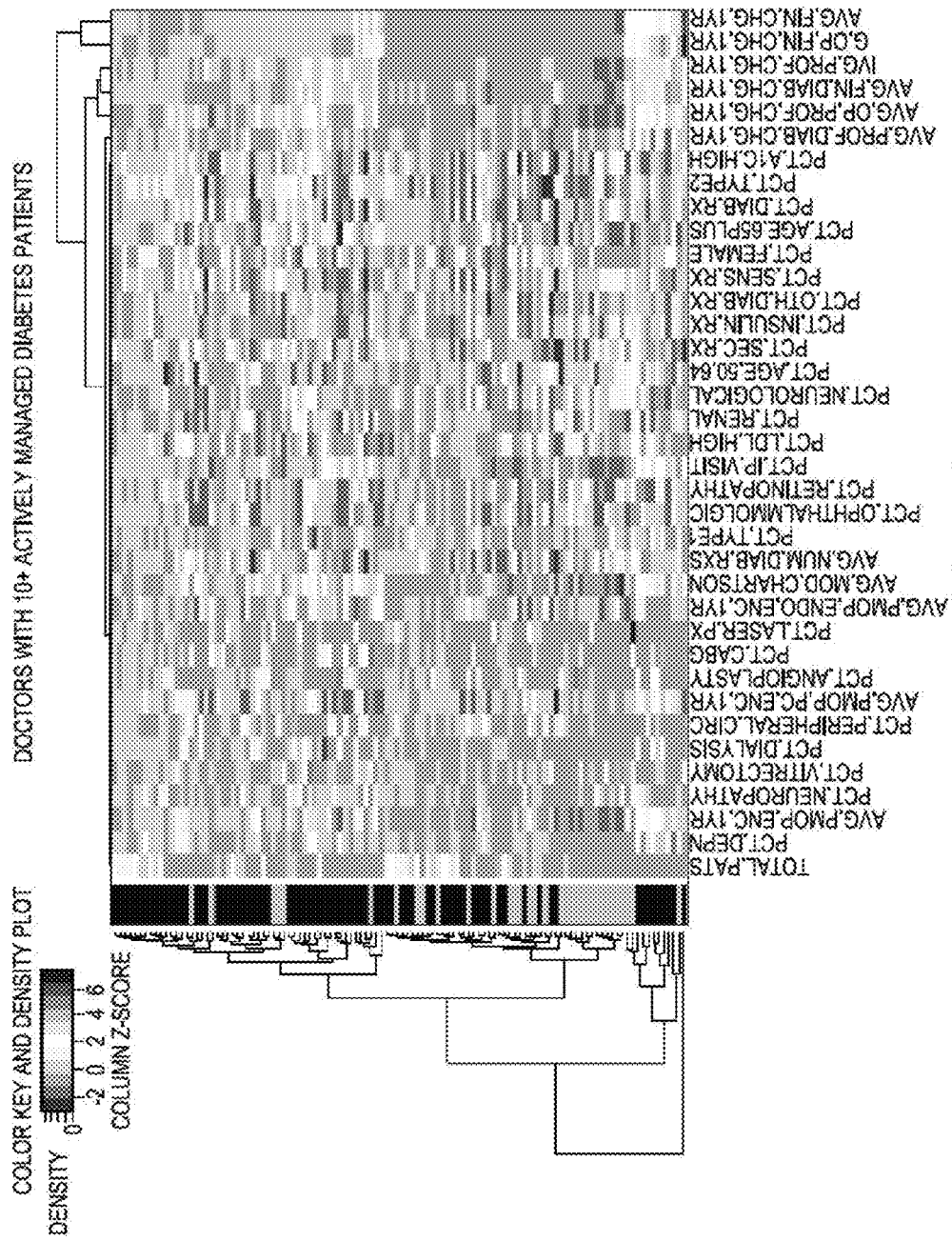
FIG. 13 depicts a heat map of doctors with 10+ actively managed diabetes patients.

Referring to FIG. 13, a heat map of doctors with 10+ actively managed diabetes patients is shown. Each column represents a particular characteristic of a physician clinical practice in the care of diabetes such as percent patients with renal failure, on insulin, with high LDL, having type 1 diabetes, with highest values in dark blue, medium values neutral, and lowest values in dark red for each measurement. An individual physician is represented by a row. The heat map is constructed using a self-organizing clustering algorithm which clusters physicians with similar characteristics clustered together vertically, and similar care characteristics clustered together horizontally. The tree structure on the far left and top of the heat map indicate the degree of similarity. The clinic to which each physician belongs is color coded as either blue or gray on the vertical column on the left of the heat map. Review of the heat map allows an administrator, physician, or nurse to identify similarities in the care of diabetes patients, and to identify key differences between individuals on particular care parameters. The heat map can identify similarities within and between clinics as well, and can identify physicians who fall outside the care characteristics of their particular clinic. Finally, by examining the clustering of care characteristics, the viewer can identify groups of care parameters that tend to be used in similar frequency by all physicians. For example, the yellow/red cluster in the lower right are all indicators of charges, with these physicians submitting charges on the lower end of their peers. An administrator could study other parameters of care to see where they differ from their peers to determine the reasons why their practices generate lower charges, on average, than other practices.

Figure 21:
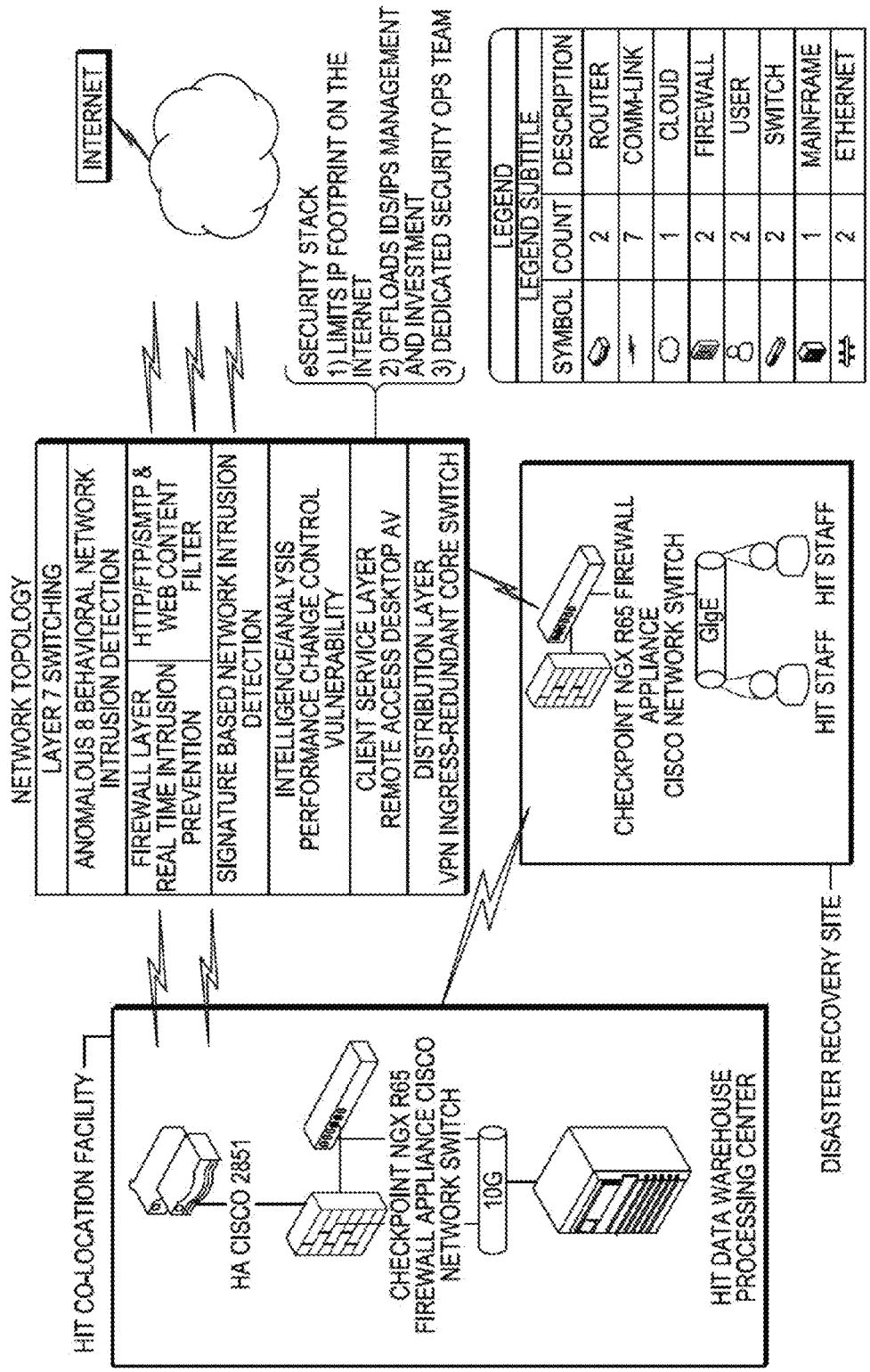
FIG. 21 depicts a network topology.

In an embodiment, the clinical analytics platform 100 may be embodied in the network topology depicted in FIG. 21. This network topology includes a distributed, layered architecture comprising intrusion protection and intrusion detection systems. Such a topology provides the security and manageability needed to deploy the platform 100 as a SaaS solution.

The methods and systems described herein may be deployed in part or in whole through a machine that executes computer software, program codes, and/or instructions on a processor. The processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipments, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

All documents referenced herein are hereby incorporated by reference.

What is claimed is:

1. A method of ingesting and analyzing healthcare data from a plurality of data sources in real-time, comprising:
   connecting to at least one data source;
   retrieving data from the data source on a periodic basis to a database;
   synchronizing data between the at least one data source and the database;
   processing the data to identify data elements, map data elements, and normalize data elements, wherein the data elements are stored in a database,
   wherein the mapping comprises assigning data to a field of a database according to a hierarchically organized lexicon of healthcare data elements, wherein multiple data element entries in the lexicon are mapped to a single field for at least one field;
   linking the data elements over time to form a longitudinal data record, wherein the longitudinal data records are stored in a longitudinal data warehouse; and
   analyzing the longitudinal data records with a computer processor to obtain a heat map, wherein one axis of the heat map relates to a health status and the other axis of the map relates to a prescribing pattern;
   wherein the colors of the plot visually indicate the quantifiable differences in prescribing for different statuses of health.

2. The method of claim 1, wherein the periodic basis on which data are retrieved is in real-time.

3. The method of claim 2, wherein realtime is at least as frequent as every five minutes.

4. The method of claim 1, wherein the at least one data source comprises doctor's notes from which data are retrieved using natural processing language.

5. The method of claim 1, wherein the at least one data source comprises at least one of an electronic medical record, an electronic health record, a patient medical record, ambulatory clinical data, claims data, paid claims data, adjudicated claims data, inpatient clinical data, pharmacy data, doctor's notes, self-reported data, census data, telemetry data, a networked monitor, a home blood pressure device, a home health monitoring device, a sensor device, mortality data, an internal management system, a hospital inventory system, a clinical inventory system, a clinical guideline, a specialty management system and an order set.

6. The method of claim 1, wherein processing the healthcare data also comprises validating the healthcare data elements.

7. The method of claim 1, wherein the health status relates to a diabetic status.

8. The method of claim 1 wherein the prescribing pattern relates to a percentage of patients treated with a particular prescription.

9. The method of claim 1 wherein analyzing further comprises producing a visualization of a referral network that identifies specialists as having at least one of a particular referral rate, care outcome and cost.

10. The method of claim 1 wherein processing to normalize data elements comprises de-identifying said data elements.

11. The method of claim 1 wherein the prescribing pattern relates to an average treatment value.

12. A method of ingesting and analyzing healthcare data from a plurality of data sources in real-time, comprising:
    connecting to at least one data source;
    retrieving data from the data source on a periodic basis to a database;
    synchronizing data between the at least one data source and the database;
    processing the data to identify data elements, map data elements, and normalize data elements, wherein the data elements are stored in a database,
    wherein the mapping comprises assigning data to a field of a database according to a hierarchically organized lexicon of healthcare data elements, wherein multiple data element entries in the lexicon are mapped to a single field for at least one field;
    linking the data elements over time to form a longitudinal data record, wherein the longitudinal data records are stored in a longitudinal data warehouse; and
    analyzing the longitudinal data records with a computer processor to obtain a co-morbidity heat map, wherein one axis of the co-morbidity heat map relates to a first health status and the other axis of the map relates to a second health status,
    wherein the colors of the plot indicate the presence of a co-morbidity.

13. The method of claim 12, wherein the colors of the plot further indicate a quantification of the co-morbidity.

14. The method of claim 12, wherein the first health status is diabetes and the second health status relates to at least one of an ophthalmic disorder, a peripheral vascular disease (PVD), a Charlson co-morbidity score, a stroke, a cardiovascular disease (CVD), a renal disease, a lipid, and hypertension (HTN).

15. A method of ingesting and analyzing healthcare data from a plurality of data sources in real-time, comprising:
- connecting to at least one data source;
- retrieving data from the data source on a periodic basis to a database;
- synchronizing data between the at least one data source and the database;
- processing the data to identify data elements, map data elements, and normalize data elements, wherein the data elements are stored in a database,
- wherein the mapping comprises assigning data to a field of a database according to a hierarchically organized lexicon of healthcare data elements, wherein multiple data element entries in the lexicon are mapped to a single field for at least one field;
- linking the data elements over time to form a longitudinal data record, wherein the longitudinal data records are stored in a longitudinal data warehouse; and
- analyzing the longitudinal data records with a computer processor to obtain a physician heat map, wherein one axis of the physician heat map represents an individual physician and the other axis of the physician heat map relates to a particular characteristic of a physician clinical practice in the care of a particular health status,
- wherein the physician heat map is constructed using a self-organizing clustering algorithm which clusters physicians with similar characteristics along one axis.

16. The method of claim 15, further comprising, the algorithm clusters care characteristics along the other axis.

17. The method of claim 15, wherein the color of the plot indicate a measurement of the particular characteristic.

18. The method of claim 15, wherein the at least one data source comprises doctor's notes from which data are retrieved using natural processing language.

19. The method of claim 15, wherein processing to normalize the data elements comprises de-identifying the data elements.

20. The method of claim 15, wherein the particular health status is diabetes and the particular characteristic relates to a charge.

* * * * *

UNITED STATES PATENT AND TRADEMARK OFFICE
CERTIFICATE OF CORRECTION

| | | |
|---|---|---|
| PATENT NO. | : 8,731,966 B2 | Page 1 of 1 |
| APPLICATION NO. | : 12/890018 | |
| DATED | : May 20, 2014 | |
| INVENTOR(S) | : Agneta Breitenstein et al. | |

It is certified that error appears in the above-identified patent and that said Letters Patent is hereby corrected as shown below:

In the Specification:

In column 3, line 59, delete "tracking" and insert --tracking.--, therefor.

In column 11, line 12, delete "tracking" and insert --tracking.--, therefor.

In column 11, line 32, delete "tracking" and insert --tracking.--, therefor.

Signed and Sealed this
Fifth Day of August, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,731,966 B2
APPLICATION NO. : 12/890018
DATED : May 20, 2014
INVENTOR(S) : Agneta Breitenstein et al.

Page 1 of 1

It is certified that error appears in the above-identified patent and that said Letters Patent is hereby corrected as shown below:

On the Title page, in item (75), under "Inventors", in column 1, line 1, delete "Agenta Breitenstein" and insert -- Agneta Breitenstein --, therefor.

Signed and Sealed this
Twenty-sixth Day of May, 2015

Michelle K. Lee
*Director of the United States Patent and Trademark Office*